US008494905B2

(12) United States Patent
Pradeep et al.

(10) Patent No.: US 8,494,905 B2
(45) Date of Patent: *Jul. 23, 2013

(54) AUDIENCE RESPONSE ANALYSIS USING SIMULTANEOUS ELECTROENCEPHALOGRAPHY (EEG) AND FUNCTIONAL MAGNETIC RESONANCE IMAGING (FMRI)

(75) Inventors: Anantha Pradeep, Berkeley, CA (US); Robert T. Knight, Berkeley, CA (US); Ramachandran Gurumoorthy, Berkeley, CA (US)

(73) Assignee: The Nielsen Company (US), LLC, Schaumburg, IL (US)

( * ) Notice: Subject to any disclaimer, the term of this patent is extended or adjusted under 35 U.S.C. 154(b) by 353 days.

This patent is subject to a terminal disclaimer.

(21) Appl. No.: 12/135,074

(22) Filed: Jun. 6, 2008

(65) Prior Publication Data

US 2009/0030303 A1   Jan. 29, 2009

Related U.S. Application Data

(60) Provisional application No. 60/942,283, filed on Jun. 6, 2007.

(51) Int. Cl.
*G06Q 30/00* (2012.01)
*G06Q 30/02* (2012.01)

(52) U.S. Cl.
CPC ............ *G06Q 30/00* (2013.01); *G06Q 30/0242* (2013.01)
USPC ..................................... 705/14.42; 705/14.52

(58) Field of Classification Search
CPC .................................................. G06Q 30/0242
USPC .......................................... 705/14.41, 14.66
See application file for complete search history.

(56) References Cited

U.S. PATENT DOCUMENTS

| 2,549,836 A | 4/1951 | McIntyre et al. |
| 3,490,439 A | 1/1970 | Rolston |
| 3,572,322 A | 3/1971 | Wade |
| 3,735,753 A | 5/1973 | Pisarski |
| 3,880,144 A | 4/1975 | Coursin et al. |

(Continued)

FOREIGN PATENT DOCUMENTS

| GB | 1374658 | 11/1974 |
| GB | 2221759 | 2/1990 |

(Continued)

OTHER PUBLICATIONS

ACNR, "Market Researchers Make Increasing Use of Brain Imaging," vol. 5, No. 3, Jul./Aug. 2005, 2 pages.

(Continued)

*Primary Examiner* — Ella Colbert
*Assistant Examiner* — Scott S Trotter
(74) *Attorney, Agent, or Firm* — Hanley, Flight & Zimmerman, LLC

(57) ABSTRACT

Neuro-response data including Electroencephalography (EEG), Functional Magnetic Resonance Imaging (fMRI) is filtered, analyzed, and combined to evaluate the effectiveness of stimulus materials such as marketing and entertainment materials. A data collection mechanism including multiple modalities such as, Electroencephalography (EEG), Functional Magnetic Resonance Imaging (fMRI), Electrooculography (EOG), Galvanic Skin Response (GSR), etc., collects response data from subjects exposed to marketing and entertainment stimuli. A data cleanser mechanism filters the response data and removes cross-modality interference.

20 Claims, 8 Drawing Sheets

U.S. PATENT DOCUMENTS

| | | | |
|---|---|---|---|
| 3,901,215 A | 8/1975 | John |
| 3,998,213 A | 12/1976 | Price |
| 4,075,657 A | 2/1978 | Weinblatt |
| 4,149,716 A | 4/1979 | Scudder |
| 4,201,224 A | 5/1980 | John |
| 4,279,258 A | 7/1981 | John |
| 4,411,273 A | 10/1983 | John |
| 4,417,592 A | 11/1983 | John |
| 4,537,198 A | 8/1985 | Corbett |
| 4,557,270 A | 12/1985 | John |
| 4,610,259 A | 9/1986 | Cohen et al. |
| 4,613,951 A | 9/1986 | Chu |
| 4,632,122 A | 12/1986 | Johansson et al. |
| 4,683,892 A | 8/1987 | Johansson et al. |
| 4,695,879 A | 9/1987 | Weinblatt |
| 4,736,751 A | 4/1988 | Gevins et al. |
| 4,800,888 A | 1/1989 | Itil et al. |
| 4,802,484 A | 2/1989 | Friedman et al. |
| 4,846,190 A | 7/1989 | John |
| 4,885,687 A | 12/1989 | Carey |
| 4,894,777 A | 1/1990 | Negishi et al. |
| 4,913,160 A | 4/1990 | John |
| 4,955,388 A | 9/1990 | Silberstein |
| 4,967,038 A | 10/1990 | Gevins et al. |
| 4,987,903 A | 1/1991 | Keppel et al. |
| 5,003,986 A | 4/1991 | Finitzo et al. |
| 5,010,891 A | 4/1991 | Chamoun |
| 5,038,782 A | 8/1991 | Gevins et al. |
| 5,052,401 A | 10/1991 | Sherwin |
| 5,083,571 A | 1/1992 | Prichep |
| RE34,015 E | 8/1992 | Duffy |
| 5,137,027 A | 8/1992 | Rosenfeld |
| 5,213,338 A | 5/1993 | Brotz |
| 5,226,177 A | 7/1993 | Nickerson |
| 5,243,517 A * | 9/1993 | Schmidt et al. ............... 600/544 |
| 5,273,037 A | 12/1993 | Itil et al. |
| 5,291,888 A | 3/1994 | Tucker |
| 5,293,867 A | 3/1994 | Oommen |
| 5,295,491 A | 3/1994 | Gevins |
| 5,339,826 A | 8/1994 | Schmidt et al. |
| 5,357,957 A | 10/1994 | Itil et al. |
| 5,363,858 A | 11/1994 | Farwell |
| 5,392,788 A | 2/1995 | Hudspeth |
| 5,406,956 A | 4/1995 | Farwell |
| 5,447,166 A | 9/1995 | Gevins |
| 5,474,082 A | 12/1995 | Junker |
| 5,479,934 A | 1/1996 | Imran |
| 5,518,007 A | 5/1996 | Becker |
| 5,537,618 A | 7/1996 | Boulton et al. |
| 5,617,855 A | 4/1997 | Waletzky et al. |
| 5,655,534 A | 8/1997 | Ilmoniemi |
| 5,676,138 A | 10/1997 | Zawilinski |
| 5,720,619 A | 2/1998 | Fisslinger |
| 5,724,987 A | 3/1998 | Gevins et al. |
| 5,729,205 A | 3/1998 | Kwon |
| 5,740,035 A | 4/1998 | Cohen et al. |
| 5,762,611 A | 6/1998 | Lewis et al. |
| 5,771,897 A | 6/1998 | Zufrin |
| 5,787,187 A | 7/1998 | Bouchard et al. |
| 5,800,351 A | 9/1998 | Mann |
| 5,812,642 A | 9/1998 | Leroy |
| 5,817,029 A | 10/1998 | Gevins et al. |
| 5,848,399 A | 12/1998 | Burke |
| 5,945,863 A | 8/1999 | Coy |
| 5,961,332 A * | 10/1999 | Joao ............................ 434/236 |
| 5,983,129 A | 11/1999 | Cowan et al. |
| 6,001,065 A | 12/1999 | DeVito |
| 6,021,346 A | 2/2000 | Ryu et al. |
| 6,052,619 A | 4/2000 | John |
| 6,099,319 A * | 8/2000 | Zaltman et al. ............... 434/236 |
| 6,120,440 A * | 9/2000 | Goknar ........................ 600/300 |
| 6,128,521 A | 10/2000 | Marro et al. |
| 6,154,669 A | 11/2000 | Hunter et al. |
| 6,155,927 A | 12/2000 | Levasseur et al. |
| 6,161,030 A | 12/2000 | Levendowski et al. |
| 6,173,260 B1 | 1/2001 | Slaney |
| 6,175,753 B1 | 1/2001 | Menkes et al. |
| 6,228,038 B1 | 5/2001 | Claessens |
| 6,236,885 B1 | 5/2001 | Hunter et al. |
| 6,254,536 B1 | 7/2001 | DeVito |
| 6,280,198 B1 * | 8/2001 | Calhoun et al. ............... 434/236 |
| 6,286,005 B1 | 9/2001 | Cannon |
| 6,289,234 B1 | 9/2001 | Mueller |
| 6,292,688 B1 | 9/2001 | Patton |
| 6,301,493 B1 | 10/2001 | Marro et al. |
| 6,315,569 B1 | 11/2001 | Zaltman |
| 6,330,470 B1 | 12/2001 | Tucker et al. |
| 6,334,778 B1 * | 1/2002 | Brown ........................ 434/258 |
| 6,374,143 B1 | 4/2002 | Berrang et al. |
| 6,381,481 B1 | 4/2002 | Levendowski et al. |
| 6,398,643 B1 | 6/2002 | Knowles et al. |
| 6,422,999 B1 | 7/2002 | Hill |
| 6,434,419 B1 | 8/2002 | Gevins et al. |
| 6,453,194 B1 | 9/2002 | Hill |
| 6,487,444 B2 | 11/2002 | Mimura |
| 6,488,617 B1 | 12/2002 | Katz |
| 6,510,340 B1 | 1/2003 | Jordan |
| 6,520,905 B1 | 2/2003 | Surve et al. |
| 6,545,685 B1 | 4/2003 | Dorbie |
| 6,575,902 B1 | 6/2003 | Burton |
| 6,577,329 B1 | 6/2003 | Flickner et al. |
| 6,585,521 B1 | 7/2003 | Obrador |
| 6,594,521 B2 | 7/2003 | Tucker |
| 6,598,006 B1 | 7/2003 | Honda et al. |
| 6,654,626 B2 | 11/2003 | Devlin et al. |
| 6,662,052 B1 | 12/2003 | Sarwal et al. |
| 6,665,560 B2 | 12/2003 | Becker et al. |
| 6,688,890 B2 | 2/2004 | von Buegner |
| 6,708,051 B1 | 3/2004 | Durousseau |
| 6,712,468 B1 | 3/2004 | Edwards |
| 6,754,524 B2 | 6/2004 | Johnson, Jr. |
| 6,757,556 B2 | 6/2004 | Gopinathan et al. |
| 6,788,882 B1 | 9/2004 | Geer et al. |
| 6,792,304 B1 | 9/2004 | Silberstein |
| 6,842,877 B2 * | 1/2005 | Robarts et al. ............... 715/708 |
| 6,904,408 B1 | 6/2005 | McCarthy et al. |
| 6,950,698 B2 | 9/2005 | Sarkela et al. |
| 6,958,710 B2 | 10/2005 | Zhang et al. |
| 6,973,342 B1 | 12/2005 | Swanson |
| 6,993,380 B1 | 1/2006 | Modarres |
| 7,130,673 B2 | 10/2006 | Tolvanen-Laakso et al. |
| 7,150,715 B2 | 12/2006 | Collura et al. |
| 7,164,967 B2 | 1/2007 | Etienne-Cummings et al. |
| 7,177,675 B2 | 2/2007 | Suffin et al. |
| 7,222,071 B2 | 5/2007 | Neuhauser et al. |
| 7,272,982 B2 | 9/2007 | Neuhauser et al. |
| 7,286,871 B2 * | 10/2007 | Cohen ........................ 600/544 |
| 7,340,060 B2 | 3/2008 | Tomkins et al. |
| 7,391,835 B1 | 6/2008 | Gross et al. |
| 7,408,460 B2 | 8/2008 | Crystal et al. |
| 7,420,464 B2 | 9/2008 | Fitzgerald et al. |
| 7,443,292 B2 | 10/2008 | Jensen et al. |
| 7,460,827 B2 | 12/2008 | Schuster et al. |
| 7,463,143 B2 | 12/2008 | Forr et al. |
| 7,463,144 B2 | 12/2008 | Crystal et al. |
| 7,471,987 B2 | 12/2008 | Crystal et al. |
| 7,483,835 B2 | 1/2009 | Neuhauser et al. |
| 7,496,400 B2 | 2/2009 | Hoskonen et al. |
| 7,548,774 B2 | 6/2009 | Kurtz et al. |
| 7,551,952 B2 | 6/2009 | Gevins et al. |
| 7,592,908 B2 | 9/2009 | Zhang et al. |
| 7,614,066 B2 | 11/2009 | Urdang et al. |
| 7,623,823 B2 | 11/2009 | Zito et al. |
| 7,636,456 B2 | 12/2009 | Collins et al. |
| 7,650,793 B2 | 1/2010 | Jensen et al. |
| 7,689,272 B2 | 3/2010 | Farwell |
| 7,697,979 B2 | 4/2010 | Martinerie et al. |
| 7,698,238 B2 | 4/2010 | Barletta et al. |
| 7,720,351 B2 | 5/2010 | Levitan |
| 7,729,755 B2 | 6/2010 | Laken |
| 7,809,420 B2 | 10/2010 | Hannula et al. |
| 7,840,248 B2 | 11/2010 | Fuchs et al. |
| 7,840,250 B2 | 11/2010 | Tucker |
| 7,865,394 B1 | 1/2011 | Calloway |
| 7,892,764 B2 | 2/2011 | Xiong et al. |
| 7,908,133 B2 | 3/2011 | Neuhauser |
| 7,917,366 B1 | 3/2011 | Levanon et al. |

| | | |
|---|---|---|
| 7,962,315 B2 | 6/2011 | Jensen et al. |
| 7,988,557 B2 | 8/2011 | Soderlund |
| 8,014,847 B2 * | 9/2011 | Shastri et al. ............... 600/410 |
| 8,098,152 B2 | 1/2012 | Zhang et al. |
| 8,135,606 B2 | 3/2012 | Dupree |
| 8,165,916 B2 | 4/2012 | Hoffberg et al. |
| 8,209,224 B2 | 6/2012 | Pradeep et al. |
| 8,229,469 B2 | 7/2012 | Zhang et al. |
| 8,239,030 B1 | 8/2012 | Hagedorn et al. |
| 8,255,267 B2 | 8/2012 | Breiter |
| 8,270,814 B2 | 9/2012 | Pradeep et al. |
| 8,327,395 B2 | 12/2012 | Lee |
| 8,332,883 B2 | 12/2012 | Lee |
| 8,335,715 B2 | 12/2012 | Pradeep et al. |
| 8,386,312 B2 | 2/2013 | Pradeep et al. |
| 8,386,313 B2 | 2/2013 | Pradeep et al. |
| 8,388,165 B2 | 3/2013 | Zhang |
| 8,392,250 B2 | 3/2013 | Pradeep et al. |
| 8,392,251 B2 | 3/2013 | Pradeep et al. |
| 8,392,253 B2 | 3/2013 | Pradeep et al. |
| 8,392,254 B2 | 3/2013 | Pradeep et al. |
| 8,392,255 B2 | 3/2013 | Pradeep et al. |
| 8,396,744 B2 | 3/2013 | Pradeep et al. |
| 2001/0020236 A1 | 9/2001 | Cannon |
| 2001/0056225 A1 | 12/2001 | DeVito |
| 2002/0065826 A1 | 5/2002 | Bell et al. |
| 2002/0072952 A1 | 6/2002 | Hamzey et al. |
| 2002/0077534 A1 | 6/2002 | DuRousseau |
| 2002/0155878 A1 | 10/2002 | Lert, Jr. et al. |
| 2002/0156842 A1 | 10/2002 | Signes et al. |
| 2002/0188216 A1 | 12/2002 | Kayyali et al. |
| 2002/0188217 A1 | 12/2002 | Farwell |
| 2002/0193670 A1 | 12/2002 | Garfield et al. |
| 2003/0013981 A1 * | 1/2003 | Gevins et al. ............... 600/544 |
| 2003/0036955 A1 | 2/2003 | Tanaka et al. |
| 2003/0059750 A1 * | 3/2003 | Bindler et al. ............... 434/236 |
| 2003/0073921 A1 | 4/2003 | Sohmer et al. |
| 2003/0100998 A2 | 5/2003 | Brunner et al. |
| 2003/0104865 A1 | 6/2003 | Itkis et al. |
| 2003/0165270 A1 | 9/2003 | Endrikhovski et al. |
| 2003/0177488 A1 | 9/2003 | Smith et al. |
| 2003/0233278 A1 | 12/2003 | Marshall |
| 2004/0005143 A1 | 1/2004 | Tsuru et al. |
| 2004/0013398 A1 | 1/2004 | Miura et al. |
| 2004/0015608 A1 | 1/2004 | Ellis et al. |
| 2004/0073129 A1 | 4/2004 | Caldwell et al. |
| 2004/0092809 A1 | 5/2004 | DeCharms |
| 2004/0098298 A1 | 5/2004 | Yin |
| 2004/0187167 A1 | 9/2004 | Maguire et al. |
| 2004/0210159 A1 * | 10/2004 | Kibar ............... 600/558 |
| 2004/0220483 A1 | 11/2004 | Yeo et al. |
| 2004/0236623 A1 | 11/2004 | Gopalakrishnan |
| 2005/0010475 A1 | 1/2005 | Perkowski et al. |
| 2005/0076359 A1 | 4/2005 | Pierson et al. |
| 2005/0079474 A1 | 4/2005 | Lowe |
| 2005/0097594 A1 | 5/2005 | O'Donnell et al. |
| 2005/0107716 A1 | 5/2005 | Eaton et al. |
| 2005/0143629 A1 | 6/2005 | Farwell |
| 2005/0154290 A1 | 7/2005 | Langleben |
| 2005/0177058 A1 | 8/2005 | Sobell |
| 2005/0197590 A1 | 9/2005 | Osorio et al. |
| 2005/0203798 A1 | 9/2005 | Jensen et al. |
| 2005/0223237 A1 | 10/2005 | Barletta et al. |
| 2005/0227233 A1 * | 10/2005 | Buxton et al. ............... 435/6 |
| 2005/0240956 A1 | 10/2005 | Smith et al. |
| 2005/0272017 A1 | 12/2005 | Neuhauser et al. |
| 2005/0273017 A1 | 12/2005 | Gordon |
| 2005/0273802 A1 | 12/2005 | Crystal et al. |
| 2005/0288954 A1 | 12/2005 | McCarthy et al. |
| 2005/0289582 A1 | 12/2005 | Tavares et al. |
| 2006/0003732 A1 | 1/2006 | Neuhauser et al. |
| 2006/0035707 A1 | 2/2006 | Nguyen et al. |
| 2006/0053110 A1 | 3/2006 | McDonald et al. |
| 2006/0093998 A1 | 5/2006 | Vertegaal |
| 2006/0111044 A1 | 5/2006 | Keller |
| 2006/0111644 A1 | 5/2006 | Guttag et al. |
| 2006/0129458 A1 | 6/2006 | Maggio |
| 2006/0167376 A1 | 7/2006 | Viirre et al. |
| 2006/0168613 A1 | 7/2006 | Wood et al. |
| 2006/0168630 A1 | 7/2006 | Davies |
| 2006/0256133 A1 | 11/2006 | Rosenberg |
| 2006/0257834 A1 | 11/2006 | Lee et al. |
| 2006/0259360 A1 | 11/2006 | Flinn et al. |
| 2006/0293921 A1 | 12/2006 | McCarthy et al. |
| 2007/0048707 A1 | 3/2007 | Caamano et al. |
| 2007/0055169 A1 | 3/2007 | Lee et al. |
| 2007/0060831 A1 | 3/2007 | Le et al. |
| 2007/0066874 A1 | 3/2007 | Cook |
| 2007/0066915 A1 | 3/2007 | Frei et al. |
| 2007/0066916 A1 | 3/2007 | Lemos |
| 2007/0067007 A1 | 3/2007 | Schulman et al. |
| 2007/0078706 A1 | 4/2007 | Datta et al. |
| 2007/0079331 A1 | 4/2007 | Datta et al. |
| 2007/0106170 A1 | 5/2007 | Dunseath, Jr. et al. |
| 2007/0135727 A1 | 6/2007 | Virtanen et al. |
| 2007/0135728 A1 | 6/2007 | Snyder et al. |
| 2007/0225585 A1 | 9/2007 | Washbon et al. |
| 2007/0225674 A1 | 9/2007 | Molnar et al. |
| 2007/0226760 A1 | 9/2007 | Neuhauser et al. |
| 2007/0235716 A1 | 10/2007 | Delic et al. |
| 2007/0238945 A1 | 10/2007 | Delic et al. |
| 2007/0250846 A1 | 10/2007 | Swix et al. |
| 2007/0265507 A1 | 11/2007 | de Lemos |
| 2007/0294132 A1 | 12/2007 | Zhang et al. |
| 2007/0294705 A1 | 12/2007 | Gopalakrishnan |
| 2007/0294706 A1 | 12/2007 | Neuhauser et al. |
| 2008/0001600 A1 | 1/2008 | deCharms |
| 2008/0010110 A1 | 1/2008 | Neuhauser et al. |
| 2008/0027345 A1 | 1/2008 | Kumada et al. |
| 2008/0040740 A1 | 2/2008 | Plotnick et al. |
| 2008/0059997 A1 | 3/2008 | Plotnick et al. |
| 2008/0065468 A1 | 3/2008 | Berg et al. |
| 2008/0065721 A1 | 3/2008 | Cragun |
| 2008/0081961 A1 | 4/2008 | Westbrook et al. |
| 2008/0082019 A1 | 4/2008 | Ludving et al. |
| 2008/0086356 A1 | 4/2008 | Glassman et al. |
| 2008/0091512 A1 | 4/2008 | Marci et al. |
| 2008/0097854 A1 | 4/2008 | Young |
| 2008/0109840 A1 | 5/2008 | Walter et al. |
| 2008/0125110 A1 | 5/2008 | Ritter |
| 2008/0147488 A1 | 6/2008 | Tunick et al. |
| 2008/0152300 A1 | 6/2008 | Knee et al. |
| 2008/0204273 A1 | 8/2008 | Crystal et al. |
| 2008/0208072 A1 | 8/2008 | Fadem et al. |
| 2008/0214902 A1 | 9/2008 | Lee et al. |
| 2008/0221400 A1 | 9/2008 | Lee et al. |
| 2008/0221472 A1 | 9/2008 | Lee et al. |
| 2008/0221969 A1 | 9/2008 | Lee et al. |
| 2008/0222670 A1 | 9/2008 | Lee et al. |
| 2008/0222671 A1 | 9/2008 | Lee et al. |
| 2008/0228077 A1 | 9/2008 | Wilk et al. |
| 2008/0255949 A1 | 10/2008 | Genco et al. |
| 2008/0295126 A1 | 11/2008 | Lee et al. |
| 2009/0024049 A1 | 1/2009 | Pradeep et al. |
| 2009/0024447 A1 | 1/2009 | Pradeep et al. |
| 2009/0024448 A1 | 1/2009 | Pradeep et al. |
| 2009/0024449 A1 | 1/2009 | Pradeep et al. |
| 2009/0024475 A1 | 1/2009 | Pradeep et al. |
| 2009/0025023 A1 | 1/2009 | Pradeep et al. |
| 2009/0030287 A1 | 1/2009 | Pradeep et al. |
| 2009/0030717 A1 | 1/2009 | Pradeep et al. |
| 2009/0030930 A1 | 1/2009 | Pradeep et al. |
| 2009/0036755 A1 | 2/2009 | Pradeep et al. |
| 2009/0036756 A1 | 2/2009 | Pradeep et al. |
| 2009/0037575 A1 | 2/2009 | Crystal et al. |
| 2009/0062629 A1 | 3/2009 | Pradeep et al. |
| 2009/0062680 A1 | 3/2009 | Sandford |
| 2009/0062681 A1 | 3/2009 | Pradeep et al. |
| 2009/0063255 A1 | 3/2009 | Pradeep et al. |
| 2009/0063256 A1 | 3/2009 | Pradeep et al. |
| 2009/0070798 A1 | 3/2009 | Lee et al. |
| 2009/0082643 A1 | 3/2009 | Pradeep et al. |
| 2009/0083129 A1 | 3/2009 | Pradeep et al. |
| 2009/0088610 A1 | 4/2009 | Lee et al. |
| 2009/0112077 A1 | 4/2009 | Nguyen et al. |
| 2009/0119154 A1 | 5/2009 | Jung et al. |
| 2009/0253996 A1 | 10/2009 | Lee et al. |
| 2009/0327068 A1 | 12/2009 | Pradeep et al. |

| | | | |
|---|---|---|---|
| 2009/0328089 | A1 | 12/2009 | Pradeep et al. |
| 2010/0004977 | A1 | 1/2010 | Marci et al. |
| 2010/0022821 | A1 | 1/2010 | Dubi et al. |
| 2010/0042012 | A1 | 2/2010 | Alhussiny |
| 2010/0060300 | A1 | 3/2010 | Mueller et al. |
| 2010/0125219 | A1 | 5/2010 | Harris et al. |
| 2010/0145215 | A1 | 6/2010 | Pradeep et al. |
| 2010/0180029 | A1 | 7/2010 | Fourman |
| 2010/0183279 | A1 | 7/2010 | Pradeep et al. |
| 2010/0186031 | A1 | 7/2010 | Pradeep et al. |
| 2010/0186032 | A1 | 7/2010 | Pradeep et al. |
| 2010/0198042 | A1 | 8/2010 | Popescu et al. |
| 2010/0214318 | A1 | 8/2010 | Pradeep et al. |
| 2010/0215289 | A1 | 8/2010 | Pradeep et al. |
| 2010/0218208 | A1 | 8/2010 | Holden |
| 2010/0249538 | A1 | 9/2010 | Pradeep et al. |
| 2010/0249636 | A1 | 9/2010 | Pradeep et al. |
| 2010/0250325 | A1 | 9/2010 | Pradeep et al. |
| 2010/0257052 | A1 | 10/2010 | Zito et al. |
| 2010/0306120 | A1 | 12/2010 | Ciptawilangga |
| 2010/0325660 | A1 | 12/2010 | Holden |
| 2011/0046473 | A1 | 2/2011 | Pradeep et al. |
| 2011/0046502 | A1 | 2/2011 | Pradeep et al. |
| 2011/0046503 | A1 | 2/2011 | Pradeep et al. |
| 2011/0046504 | A1 | 2/2011 | Pradeep et al. |
| 2011/0047121 | A1 | 2/2011 | Pradeep et al. |
| 2011/0059422 | A1 | 3/2011 | Masaoka |
| 2011/0105937 | A1 | 5/2011 | Pradeep et al. |
| 2011/0106621 | A1 | 5/2011 | Pradeep et al. |
| 2011/0106750 | A1 | 5/2011 | Pradeep et al. |
| 2011/0119124 | A1 | 5/2011 | Pradeep et al. |
| 2011/0119129 | A1 | 5/2011 | Pradeep et al. |
| 2011/0191142 | A1 | 8/2011 | Huang |
| 2011/0208515 | A1 | 8/2011 | Neuhauser |
| 2011/0237971 | A1 | 9/2011 | Pradeep et al. |
| 2011/0248729 | A2 | 10/2011 | Mueller et al. |
| 2011/0270620 | A1 | 11/2011 | Pradeep et al. |
| 2011/0276504 | A1 | 11/2011 | Pradeep et al. |
| 2011/0282231 | A1 | 11/2011 | Pradeep et al. |
| 2011/0282232 | A1 | 11/2011 | Pradeep et al. |
| 2011/0282749 | A1 | 11/2011 | Pradeep et al. |
| 2011/0301431 | A1 | 12/2011 | Greicius |
| 2012/0036004 | A1 | 2/2012 | Pradeep et al. |
| 2012/0036005 | A1 | 2/2012 | Pradeep et al. |
| 2012/0054018 | A1 | 3/2012 | Pradeep et al. |
| 2012/0072289 | A1 | 3/2012 | Pradeep et al. |
| 2012/0108995 | A1 | 5/2012 | Pradeep et al. |
| 2012/0114305 | A1 | 5/2012 | Holden |
| 2012/0245978 | A1 | 9/2012 | Crystal et al. |
| 2013/0060125 | A1 | 3/2013 | Zeman |

FOREIGN PATENT DOCUMENTS

| | | |
|---|---|---|
| WO | 95-18565 | 7/1995 |
| WO | 97/17774 | 5/1997 |
| WO | 97/40745 | 11/1997 |
| WO | 97/41673 | 11/1997 |
| WO | 02-100241 | 12/2002 |
| WO | 02-102238 | 12/2002 |
| WO | 2004/049225 | 6/2004 |
| WO | 2008/121651 | 10/2008 |
| WO | 2008-141340 | 10/2008 |
| WO | 2008/137579 | 11/2008 |
| WO | 2008-137581 | 11/2008 |
| WO | 2008/154410 | 12/2008 |
| WO | 2009/018374 | 2/2009 |
| WO | 2009/052833 | 4/2009 |

OTHER PUBLICATIONS

Sutherland, Max, "Neuromarketing: What's It All About?" From Max Sutherland's Weblog at www.sutherlandsurvey.com, Feb. 2007, p. 1-5.

Haq Amber, "This is Your Brain on Advertising," Business Week, Market Research, Oct. 8, 2007, 2 pages.

Barcelo, Francisco, et al., "Prefrontal Modulation of Visual Processing in Humans," Nature Neuroscience, vol. 3, No. 4, Apr. 2000, pp. 399-403.

Canolty, R.T., et al., "High Gamma Power Is Phase-Locked to Theta Oscillations in Human Neocortex," Science, vol. 313, Sep. 15, 2006, pp. 1626-1628.

Engel, Andreas, et al., "Dynamic Predictions: Oscillations and Synchrony in Top-Down Processing," Macmillan Magazines Ltd, vol. 2, Oct. 2001, pp. 704-716.

Fries, Pascal, "A Mechanism for Cognitive Dynamics: Neuronal Communication Through Neuronal Coherence," Trends in Cognitive Sciences, vol. 9, No. 10, Oct. 2005, p. 474-480.

Gazzaley, Adam, et al., "Top-down Enhancement and Suppression of the Magnitude and Speed of Neural Activity," Journal of Cognitive Neuroscience, vol. 17, No. 3, pp. 507-517.

Hartikainen, Kaisa, et al., "Emotionally Arousing Stimuli Compete with Attention to Left Hemispace," Editorial Manager(tm) for NeuroReport, Manuscript Draft, Manuscript No. NR-D-07-5935R1, submitted Sep. 8, 2007, 26 pages.

Knight, Robert T., "Contribution of Human Hippocampal Region to Novelty Detection," Nature, vol. 383, Sep. 19, 1996, p. 256-259.

Knight Robert T., "Decreased Response to Novel Stimuli After Prefrontal Lesions in Man," Electroencephalography and Clinical Neurophysiology, vol. 59, 1984, pp. 9-20.

Miltner, Wolfgang H.R., et al., "Coherence of Gamma-band EEG Activity as a Basis for Associative Learning," Nature, vol. 397, Feb. 4, 1999, pp. 434-436.

EEG Protocols, Protocols for EEG Recording, Nov. 13, 2007, 3 pages.

Nielsen, Finn Arup, Neuroinformatics in Functional Neuroimaging, Information and Mathematical Modeling Technical University of Denmark, Aug. 30, 2002, 241 pages.

Final Rejection, issued by the United States Patent and Trademark Office in connection with U.S. Appl. No. 12/056,211, on Jul. 8, 2011, 16 pages.

Office Action, issued by the United States Patent and Trademark Office in connection with U.S. Appl. No. 12/056,211, on Jan. 7, 2011, 19 pages.

Office Action issued by the United States Patent and Trademark Office in connection with U.S. Appl. No. 12/056,221, on Apr. 15, 2011, 24 pages.

Final Rejection, issued by the United States Patent and Trademark Office in connection with U.S. Appl. No. 12/113,863, on Jun. 9, 2011, 12 pages.

Office Action, issued by the United States Patent and Trademark Office in connection with U.S. Appl. No. 12/113,863, on Dec. 27, 2010, 15 pages.

Final Rejection, issued by the United States Patent and Trademark Office in connection with U.S. Appl. No. 12/113,870, on Apr. 21, 2011, 10 pages.

Office Action, issued by the United States Patent and Trademark Office in connection with U.S. Appl. No. 12/113,870, on Dec. 3, 2010, 12 pages.

Office Action, issued by the United States Patent and Trademark Office in connection with U.S. Appl. No. 12/122,240, on Jun. 10, 2011, 12 pages.

Final Rejection, issued by the United States Patent and Trademark Office in connection with U.S. Appl. No. 12/122,262, on May 26, 2011, 15 pages.

Office Action, issued by the United States Patent and Trademark Office in connection with U.S. Appl. No. 12/122,262, on Dec. 9, 2010, 13 pages.

Final Rejection, issued by the United States Patent and Trademark Office in connection with U.S. Appl. No. 12/135,066, on Jan. 21, 2011, 16 pages.

Office Action, issued by the United States Patent and Trademark Office in connection with U.S. Appl. No. 12/135,066, on Oct. 28, 2010, 14 pages.

Notice of Panel Decision from Pre-Appeal Brief Review, issued by the United States Patent and Trademark Office in connection with U.S. Appl. No. 12/135,066, on May 31, 2011, 2 pages.

Final Rejection, issued by the United States Patent and Trademark Office in connection with U.S. Appl. No. 12/182,874, on Jul. 7, 2011, 14 pages.

Office Action, issued by the United States Patent and Trademark Office in connection with U.S. Appl. No. 12/182,874, on Dec. 27, 2010, 17 pages.
Office Action, issued by the United States Patent and Trademark Office in connection with U.S. Appl. No. 12/199,557, on Dec. 27, 2010, 14 pages.
Final Rejection, issued by the United States Patent and Trademark Office in connection with U.S. Appl. No. 12/199,557, on Jun. 9, 2011, 12 pages.
Final Rejection, issued by the United States Patent and Trademark Office in connection with U.S. Appl. No. 12/199,583, on Jun. 21, 2011, 14 pages.
Office Action, issued by the United States Patent and Trademark Office in connection with U.S. Appl. No. 12/199,583, on Dec. 27, 2010, 17 pages.
Final Rejection, issued by the United States Patent and Trademark Office in connection with U.S. Appl. No. 12/199,596, on Jun. 14, 2011, 13 pages.
Office Action, issued by the United States Patent and Trademark Office in connection with U.S. Appl. No. 12/199,596, on Dec. 27, 2010, 17 pages.
Final Rejection, issued by the United States Patent and Trademark Office in connection with U.S. Appl. No. 12/200,813, on Jul. 6, 2011, 13 pages.
Office Action, issued by the United States Patent and Trademark Office in connection with U.S. Appl. No. 12/200,813, on Dec. 27, 2010, 14 pages.
Office Action, issued by the United States Patent and Trademark Office in connection with U.S. Appl. No. 12/234,372, on Jun. 7, 2011, 10 pages.
Final Rejection, issued by the United States Patent and Trademark Office in connection with U.S. Appl. No. 12/135,069, on Feb. 17, 2011, 32 pages.
Office Action, issued by the United States Patent and Trademark Office in connection with U.S. Appl. No. 12/135,069, on Oct. 29, 2010, 21 pages.
Office Action, issued by the United States Patent and Trademark Office in connection with U.S. Appl. No. 12/357,315, on May 4, 2011, 9 pages.
Office Action, issued by the United States Patent and Trademark Office in connection with U.S. Appl. No. 12/410,380, on Jun. 7, 2011, 9 pages.
Office Action, issued by the United States Patent and Trademark Office in connection with U.S. Appl. No. 12/413,297, on Jul. 18, 2011, 9 pages.
Office Action, issued by the United States Patent and Trademark Office in connection with U.S. Appl. No. 12/608,685, on Jul. 12, 2011, 15 pages.
Office Action, issued by the United States Patent and Trademark Office in connection with U.S. Appl. No. 12/056,190, on Aug. 10, 2011, 28 pages.
Office Action, issued by the United States Patent and Trademark Office in connection with U.S. Appl. No. 12/357,322, on Aug. 23, 2011, 12 pages.
Office Action, issued by the United States Patent and Trademark Office in connection with U.S. Appl. No. 12/135,069, on Aug. 26, 2011, 33 pages.
Restriction Requirement, issued by the United States Patent and Trademark Office in connection with U.S. Appl. No. 12/122,253, on Sep. 2, 2011, 7 pages.
Office Action, issued by the United States Patent and Trademark Office in connection with U.S. Appl. No. 12/410,372, on Sep. 12, 2011, 12 pages.
Restriction Requirement, issued by the United States Patent and Trademark Office in connection with U.S. Appl. No. 12/182,851, on Sep. 12, 2011, 7 pages.
Office Action, issued by the United States Patent and Trademark Office in connection with U.S. Appl. No. 12/135,066, on Sep. 29, 2011, 37 pages.
Restriction Requirement, issued by the United States Patent and Trademark Office in connection with U.S. Appl. No. 12/056,225, on Oct. 3, 2011, 6 pages.
Office Action, issued by the United States Patent and Trademark Office in connection with U.S. Appl. No. 12/234,388, on Oct. 12, 2011, 27 pages.
Office Action, issued by the United States Patent and Trademark Office in connection with U.S. Appl. No. 12/234,372, on Oct. 13, 2011, 22 pages.
Office Action, issued by the United States Patent and Trademark Office in connection with U.S. Appl. No. 12/410,380, on Oct. 19, 2011, 21 pages.
Office Action, issued by the United States Patent and Trademark Office in connection with U.S. Appl. No. 12/357,315, on Oct. 26, 2011, 41 pages.
Office Action, issued by the United States Patent and Trademark Office in connection with U.S. Appl. No. 12/122,240, on Oct. 27, 2011, 39 pages.
International Preliminary Report on Patentability, issued by the International Bureau of WIPO in connection with International Application No. PCT/US08/058264, on Sep. 29, 2009, 1 page.
International Search Report, issued by the International Searching Authority in connection with International Application No. PCT/US08/058264, on Aug. 1, 2008, 2 pages.
Written Opinion, issued by the International Searching Authority in connection with International Application No. PCT/US08/058264, on Aug. 1, 2008, 5 pages.
International Preliminary Report on Patentability, issued by the International Bureau of WIPO in connection with International Application No. PCT/US08/062273, on Nov. 3, 2009, 1 page.
International Search Report, issued by the International Searching Authority in connection with International Application No. PCT/US08/062273, on Sep. 5, 2008, 2 pages.
Written Opinion, issued by the International Searching Authority in connection with International Application No. PCT/US08/062273, on Sep. 5, 2008, 4 pages.
International Preliminary Report on Patentability, issued by the International Bureau of WIPO in connection with International Application No. PCT/US08/062275, on Nov. 3, 2009, 1 page.
International Search Report, issued by the International Bureau in connection with International Application No. PCT/US08/062275, on Sep. 22, 2008, 2 pages.
Written Opinion, issued by the International Bureau in connection with International Application No. PCT/US08/062275, on Sep. 22, 2008, 6 pages.
International Preliminary Report on Patentability, issued by the International Bureau of WIPO in connection with International Application No. PCT/US08/063984, on Nov. 17, 2009, 1 page.
International Search Report, issued by the International Bureau in connection with International Application No. PCT/US08/063984, on Sep. 29, 2008, 3 pages.
Written Opinion, issued by the International Bureau in connection with International Application No. PCT/US08/063984, on Sep. 29, 2008, 4 pages.
International Preliminary Report on Patentability, issued by the International Bureau of WIPO in connection with International Application No. PCT/US08/063989, on Nov. 17, 2009, 1 page.
International Search Report, issued by the International Bureau in connection with International Application No. PCT/US08/063989, on Jul. 17, 2008, 2 pages.
Written Opinion, issued by the International Bureau in connection with International Application No. PCT/US08/063989, on Jul. 17, 2008, 4 pages.
International Preliminary Report on Patentability, issued by the International Bureau of WIPO in connection with International Application No. PCT/US08/066166, on Dec. 7, 2009, 1 page.
International Search Report, issued by the International Bureau in connection with International Application No. PCT/US08/066166, on Aug. 25, 2008, 2 pages.
Written Opinion, issued by the International Bureau in connection with International Application No. PCT/US08/066166, on Aug. 25, 2008, 6 pages.
International Preliminary Report on Patentability, issued by the International Bureau of WIPO in connection with International Application No. PCT/US08/071639, on Feb. 2, 2010, 1 page.

International Search Report, issued by the International Bureau in connection with International Application No. PCT/US08/071639, on Oct. 22, 2008, 3 pages.

Written Opinion, issued by the International Bureau in connection with International Application No. PCT/US08/071639, on Oct. 22, 2008, 4 pages.

International Preliminary Report on Patentability, issued by the International Bureau of WIPO in connection with International Application No. PCT/US08/074467, on Mar. 2, 2010, 1 page.

International Search Report, issued by the International Bureau in connection with International Application No. PCT/US08/074467, on Nov. 17, 2008, 2 pages.

Written Opinion, issued by the International Bureau in connection with International Application No. PCT/US08/074467, on Nov. 17, 2008, 4 pages.

International Preliminary Report of Patentability, issued by the International Bureau in connection with International Application No. PCT/US10/021535, on Jul. 26, 2011, 1 page.

International Search Report, issued by the International Bureau in connection with International Application No. PCT/US10/021535, on Mar. 23, 2010, 3 pages.

Written Opinion, issued by the International Bureau in connection with International Application No. PCT/US10/021535, on Mar. 23, 2010, 4 pages.

International Preliminary Report of Patentability, issued by the International Bureau in connection with International Application No. PCT/US09/065368, on Jun. 23, 2011, 2 pages.

International Search Report, issued by the International Bureau in connection with International Application No. PCT/US09/065368, on Jan. 21, 2010, 3 pages.

Written Opinion, issued by the International Bureau in connection with International Application No. PCT/US09/065368, on Jan. 21, 2010, 7 pages.

Extended European Search Report, issued by the European Patent Office in connection with European Application No. 08744383.4-2221/2130146, on Jul. 27, 2011, 6 pages.

Extended European Search Report, issued by the European Patent Office in connection with European Application No. 10173095.0-2221, on Dec. 17, 2010, 3 pages.

Extended European Search Report, issued by the European Patent Office in connection with European Application No. 10189294.1-2221, on Mar. 21, 2011, 7 pages.

First Office Action, issued by the State Intellectual Property Office of P.R. China in connection with Patent Application No. 200880104982.1, on Jan. 25, 2011, 15 pages.

First Office Action, issued by the State Intellectual Property Office of P.R. China in connection with Patent Application No. 2008801015007, on May 25, 2011, 8 pages.

First Office Action, issued by the State Intellectual Property Office of P.R. China in connection with Patent Application No. 200880019166.0, on Jul. 22, 2011, 16 pages.

Decision of Rejection, issued by the State Intellectual Property Office of P.R. China in connection with Patent Application No. 200880104982.1, on Sep. 23, 2011, 10 pages.

Edgar, et al., "Digital Filters in ERP Research," in Event-Related Potentials: A Methods Handbook pp. 85-113, (Todd C. Handy, ed., 2005), 15 pages.

Simon-Thomas, et al, "Behavioral and Electrophysiological Evidence of a Right Hemisphere Bias for the Influence of Negative Emotion on Higher Cognition," Journal of Cognitive Neuroscience, pp. 518-529, Massachusetts Institute of Technology (2005), 12 pages.

Friedman, et al., "Event-Related Potential (ERP) Studies of Memory Encoding and Retrieval: A Selective Review," Microscopy Research and Technique 51:6-26, Wiley-Less, Inc. (2000), 23 pages.

Gaillard, "Problems and Paradigms in ERP Research," Biological Psychology, Elsevier Science Publisher B.V. (1988), 10 pages.

Hopf, et al., "Neural Sources of Focused Attention in Visual Search," Cerebral Cortex, 10:1233-1241, Oxford University Press, (Dec. 2000), 9 pages.

Swick, et al., "Contributions of Prefrontal Cortex to Recognition Memory: Electrophysiological and Behavioral Evidence," Neuropsychology, vol. 13, No. 2, pp. 155-170, American Psychological Association, Inc. (1999), 16 pages.

Luck, et al., "The sped of visual attention in schizophrenia: Electrophysiological and behavioral evidence," Schizophrenia Research, pp. 174-195, Elsevier B.V. www.sciencedirect.com, (2006), 22 pages.

Makeig, et al., "Mining event-related brain dynamics," TRENDS in Cognitive Sciences, vol. 8, No. 5, (May 2004), www.sciencedirect.com, 7 pages.

Herrmann, et al., "Mechanisms of human attention: event-related potentials and oscillations," Neuroscience and Biobehavioral Reviews, pp. 465-476, Elsevier Science Ltd., www.elsevier.com/locate/neubiorev, (2001), 12 pages.

Paller, et al., "Validating neural correlates of familiarity," TRENDS in Cognitive Sciences, vol. 11, No. 6, www.sciencedirect.com, (May 2, 2007), 8 pages.

Picton, et al., "Guidelines for using human event-related potentials to study cognition: Recording standards and publication criteria," Psychophysiology, pp. 127-152, Society for Psychophysiological Research, (2000), 26 pages.

Yamaguchi, et al., "Rapid-Prefrontal—Hippocampal Habituation to Novel Events," The Journal of Neuroscience, pp. 5356-5363, Society for Neuroscience, (Apr. 29, 2004), 8 pages.

Rugg, et al., "Event-related potentials and recognition memory," TRENDS in Cognitive Sciences, vol. 11, No. 6, www.sciencedirect.com, (May 3, 2007), 7 pages.

Rugg, et al., "The ERP and cognitive psychology: conceptual issues," (Sep. 1996), 7 pages.

Spencer, "Averaging, Detection, and Classification of Single-Trial ERPs," in Event-Related Potentials: A Methods Handbook, pp. 209-227, (Todd C. Handy, ed., 2005), 10 pages.

Srinivasan, "High-Resolution EEG: Theory and Practice," in Event-Related Potentials: A Methods Handbook, pp. 167-188, (Todd C. Handy, ed., 2005), 12 pages.

Taheri, et al., "A dry electrode for EEG recording," Electroencephalography and clinical Neurophysiology, pp. 376-383, Elsevier Science Ireland Ltd. (1994), 8 pages.

Talsma, et al., "Methods for the Estimation and Removal of Artifacts and Overlap in ERP Waveforms," in Event-Related Potentials: A Methods Handbook, pp. 115-148, (Todd C. Handy, ed., 2005), 22 pages.

Davidson, et al., "The functional neuroanatomy of emotion and affective style," TRENDS in Cognitive Sciences, vol. 3, No. 1, (Jan. 1999), 11 pages.

Vogel, et al., "Electrophysiological Evidence for a Postperceptual Locus of Suppression During the Attentional Blink," Journal of Experimental Psychology: Human Perception and Performance, vol. 24, No. 6, pp. 1656-1674, (1998), 19 pages.

Rizzolatti et al., "The Mirror-Neuron System," Annu. Rev. Neurosci., vol. 27, pp. 169-192, (Mar. 5, 2004), 30 pages.

Woldorf, "Distortion of ERP averages due to overlap from temporally adjacent ERPs: Analysis and correction," Psychophysiology, Society for Psychophysiological Research, Cambridge University Press (1993), 22 pages.

Woodman, et al., "Serial Deployment of Attention During Visual Search," Journal of Experimental Psychology: Human Perception and Performance, vol. 29, No. 1, pp. 121-138, American Physiological Association (2003), 18 pages.

Knight, et al., "Prefrontal cortex regulates inhibition and excitation in distributed neural networks," Acta Psychologica vol. 101, pp. 159-178, Elsevier (1999), 20 pages.

Buschman, et al., "Top-Down versus Bottom-Up Control of Attention in the Prefrontal and posterior Parietal Cortices," Science, vol. 315, www.sciencemag.org/cgi/content/full/315/5820/1860, American Association for the Advancement of Science, (2007), 4 pages.

D'Esposito, "From cognitive to neural models of working memory," Phil. Trans. R. Soc. B, doi: 10.1098/rstb.2007.2086, (Mar. 30, 2007), 12 pages.

Dien, et al., "Application of Repeated Measures ANOVA to High-Dens Dataset: A Review and Tutorial," in Event-Related Potentials: A Methods Handbook pp. 57-82, (Todd C. Handy, ed., 2005), 14 pages.

Ambler, "Salience and Choice: Neural Correlates of Shopping Decisions," Psychology & Marketing, vol. 21, No. 4, p. 247-261, Wiley Periodicals, Inc., doi: 10.1002/mar20004, (Apr. 2004), 16 pages.

Hazlett, et al., "Emotional Response to Television Commercials: Facial EMG vs. Self-Report," Journal of Advertising Research, (Apr. 1999), 17 pages.

Makeig, et al., "Dynamic Brain Sources of Visual Evoked Responses," Science, vol. 295, www.sciencemag.org, (Jan. 25, 2002), 5 pages.

Aaker et al., "Warmth in Advertising: Measurement, Impact, and Sequence Effects," Journal of Consumer Research, vol. 12, No. 4, pp. 365-381, (Mar. 1986), 17 pages.

Belch et al., "Psychophysiological and cognitive Response to Sex in Advertising," Advances in Consumer Research, vol. 9, pp. 424-427, (1982), 6 pages.

Ruchkin et al., "Modality-specific processing streams in verbal working memory: evidence from spatio-temporal patterns of brain activity," Cognitive Brain Research, vol. 6, pp. 95-113, Elsevier, (1997), 19 pages.

Page et al., "Cognitive Neuroscience, Marketing and Research," Congress 2006—Foresight—The Predictive Power of Research Conference Papers, ESOMAR Publications, (Sep. 17, 2006), 25 pages.

Braeutigam, "Neuroeconomics—From neural systems to economic behavior," Brain Research Bulletin, vol. 67, pp. 355-360, Elsevier, (2005), 6 pages.

Lee et al., "What is 'neuromarketing'? A discussion and agenda for future research," International Journal of Psychophysiology, vol. 63, pp. 199-204, Elsevier (2006), 6 pages.

Crawford et al., "Self-generated happy and sad emotions in low and highly hypnotizable persons during waking and hypnosis: laterality and regional EEG activity differences," International Journal of Psychophysiology, vol. 24, pp. 239-266, (Dec. 1996), 28 pages.

Desmet, "Measuring Emotion: Development and Application of an Instrument to Measure Emotional Responses to Products," to be published in Funology: From Usability to Enjoyment, pp. 111-123, Kluwer Academic Publishers, (Blythe et al., eds., 2004), 13 pages.

Bagozzi et al., "The Role of Emotions in Marketing," Journal of the Academy of Marketing Science, vol. 27, No. 2, pp. 184-206, Academy of Marketing Science (1999), 23 pages.

Blakeslee, "If You Have a 'Buy Button' in Your Brain, What Pushes It?" The New York Times, www.nytimes.com, (Oct. 19, 2004), 3 pages.

Osborne, "Embedded Watermarking for image Verification in Telemedicine," Thesis submitted for the degree of Doctor of Philosophy, Electrical and Electronic Engineering, University of Adelaide (2005), 219 pages.

Arousal in Sport, in Encyclopedia of Applied Psychology, vol. 1, p. 159, retrieved from Google Books, (Spielberger, ed., Elsevier Academic Press, 2004), 1 page.

Ziegenfuss, "Neuromarketing: Advertising Ethical & Medical Technology," The Brownstone Journal, vol. XII, Boston University, pp. 69-73, (May 2005), 5 pages.

Lekakos, "Personalized Advertising Services Through Hybrid Recommendation Methods: The Case of Digital Interactive Television," Department of Informatics, Cyprus University, (2004), 11 pages.

Ambler et al., "Ads on the Brain; A Neuro-Imaging Comparison of Cognitive and Affective Advertising Stimuli," London Business School, Centre for Marketing Working Paper, No. 00-902, (Mar. 2000), 23 pages.

U.S. Appl. No. 13/045,457, filed Mar. 10, 2011, (unpublished).
U.S. Appl. No. 12/778,810, filed May 12, 2010, (unpublished).
U.S. Appl. No. 12/778,828, filed May 12, 2010, (unpublished).
U.S. Appl. No. 13/104,821, filed May 10, 2011, (unpublished).
U.S. Appl. No. 13/104,840, filed May 10, 2011, (unpublished).
U.S. Appl. No. 12/853,197, filed Aug. 9, 2010, (unpublished).
U.S. Appl. No. 12/884,034, filed Sep. 16, 2010, (unpublished).
U.S. Appl. No. 12/868,531, filed Aug. 25, 2010, (unpublished).
U.S. Appl. No. 12/913,102, filed Oct. 27, 2010, (unpublished).
U.S. Appl. No. 12/853,213, filed Aug. 9, 2010, (unpublished).
U.S. Appl. No. 13/105,774, filed May 11, 2011, (unpublished).

Klimesch, "EEG alpha and theta oscillations reflect cognitive and memory performanceJul. 20, 2012 a review and analysis," Brain Research Reviews, vol. 29, 169-195, (1999), 27 pages.

Second Office Action, issued by the State Intellectual Property Office of P.R. China in connection with Patent Application No. 200880104982.1, on Jun. 29, 2012, 5 pages.

Office Action, issued by the United States Patent and Trademark Office in connection with U.S. Appl. No. 12/868,531, on Mar. 1, 2012, 6 pages.

Office Action, issued by the United States Patent and Trademark Office in connection with U.S. Appl. No. 12/182,851, on Mar. 12, 2012, 14 pages.

Office Action, issued by the United States Patent and Trademark Office in connection with U.S. Appl. No. 12/608,685, on Mar. 29, 2012, 17 pages.

Office Action, issued by the United States Patent and Trademark Office in connection with U.S. Appl. No. 12/846,242, on Mar. 29, 2012, 15 pages.

Office Action, issued by the United States Patent and Trademark Office in connection with U.S. Appl. No. 12/234,388, on Apr. 6, 2012, 6 pages.

Office Action, issued by the United States Patent and Trademark Office in connection with U.S. Appl. No. 12/357,315, on Apr. 9, 2012, 17 pages.

Office Action, issued by the United States Patent and Trademark Office in connection with U.S. Appl. No. 12/544,958, on May 2, 2012, 14 pages.

English Translation of Office Action, issued by the Israel Patent Office in connection with Patent Application No. 203176, on Feb. 21, 2012, 2 pages.

English Translation of Office Action, issued by the Israel Patent Office in connection with Patent Application No. 203177, on Mar. 1, 2012, 2 pages.

Second Office Action, issued by the State Intellectual Property Office of P.R. China in connection with Patent Application No. 200880101500.7, on Apr. 5, 2012, 5 pages.

Padgett et al., "Categorical Perception in Facial Emotion Classification," in Proceedings of the 18th Annual Conference of the Cognitive Science Society, pp. 249-253 (1996), 5 pages.

de Gelder et al., "Categorical Perception of Facial Expressions: Categories and their Internal Structure," Cognition and Emotion, vol. 11(1), pp. 1-23 (1997), 23 pages.

Bimler et al., "Categorical perception of facial expressions of emotion: Evidence from multidimensional scaling," Cognition and Emotion, vol. 15(5), pp. 633-658 (Sep. 2001), 26 pages.

Newell et al., "Categorical perception of familiar objects," Cognition, vol. 85, Issue 2, pp. 113-143 (Sep. 2002), 31 pages.

Meriam Webster Online Dictionary, Definition of Virtual Reality, available at http://www.meriam-webster.com/dictionary/virtual%20reality, 2 page.

Griss et al., "Characterization of micromachined spiked biopotential electrodes," Biomedical Engineering, IEEE Transactions (Jun. 2002), 8 pages.

"User monitoring," Sapien Systems, available at http://web.archive.org/web/20030818043339/http:/www.sapiensystems.com/eyetracking.html, (Aug. 18, 2003), 1 page.

Notice of Allowance, issued by the United States Patent and Trademark Office in connection with U.S. Appl. No. 12/357,302, on May 7, 2012, 16 pages.

Notice of Allowance, issued by the United States Patent and Trademark Office in connection with U.S. Appl. No. 12/868,531, on May 8, 2012, 16 pages.

Notice of Allowance, issued by the United States Patent and Trademark Office in connection with U.S. Appl. No. 12/608,696, on May 15, 2012, 16 pages.

Restriction Requirement, issued by the United States Patent and Trademark Office in connection with U.S. Appl. No. 12/545,455, on Jun. 13, 2012, 5 pages.

Office Action, issued by the United States Patent and Trademark Office in connection with U.S. Appl. No. 12/056,225, on Jun. 15, 2012, 9 pages.

Office Action, issued by the United States Patent and Trademark Office in connection with U.S. Appl. No. 12/544,934, on Jun. 18, 2012, 11 pages.

Office Action, issued by the United States Patent and Trademark Office in connection with U.S. Appl. No. 12/135,066, on Jun. 21, 2012, 9 pages.
Final Rejection, issued by the United States Patent and Trademark Office in connection with U.S. Appl. No. 12/608,660, on Jul. 10, 2012, 13 pages.
Second Office Action, issued by the State Intellectual Property Office of P.R. China in connection with Patent Application No. 200880019166.0, on Jun. 5, 2012, 8 pages.
Barreto et al., "Physiologic Instrumentation for Real-time Monitoring of Affective State of Computer Users," WSEAS International Conference on Instrumentation, Measurement, Control, Circuits and Systems (IMCCAS), (2004), 6 pages.
Jung et al., "Analysis and Visualization of Single-Trial Event-Related Potentials," Human Brain Mapping vol. 14, 166-185 (2001), 20 pages.
Krugman, "Brain Wave Measures of Media Involvement," Journal of Advertising Research vol. 11, 3-9 (Feb. 1971), 7 pages.
The Mathworks, Inc., "MATLAB Data Analysis: Version 7," p. 4-19 (2005), 3 pages.
Krakow et al., "Methodology: EEG-correlated fMRI," Functional Imaging in the Epilepsies, (Lippincott Williams & Wilkins, 2000), 17 pages.
Allen et al., "A Method of Removing Imaging Artifact from Continuous EEG Recorded during Functional MRI," Neuroimage, vol. 12, 230-239, (Aug. 2000).
Office Action, issued by the United States Patent and Trademark Office in connection with U.S. Appl. No. 12/544,921, on Jan. 9, 2012, 13 pages.
Office Action, issued by the United States Patent and Trademark Office in connection with U.S. Appl. No. 12/357,302, on Jan. 17, 2012, 11 pages.
Office Action, issued by the United States Patent and Trademark Office in connection with U.S. Appl. No. 12/056,225, on Jan. 20, 2012, 12 pages.
Final Rejection, issued by the United States Patent and Trademark Office in connection with U.S. Appl. No. 12/135,066, on Jan. 24, 2012, 12 pages.
Office Action, issued by the United States Patent and Trademark Office in connection with U.S. Appl. No. 12/546,586, on Feb. 1, 2012, 17 pages.
Restriction Requirement, issued by the United States Patent and Trademark Office in connection with U.S. Appl. No. 12/544,958, on Feb. 10, 2012, 6 pages.
Final Rejection, issued by the United States Patent and Trademark Office in connection with U.S. Appl. No. 12/135,069, on Feb. 14, 2012, 35 pages.
Final Rejection, issued by the United States Patent and Trademark Office in connection with U.S. Appl. No. 12/357,322, on Feb. 14, 2012, 14 pages.
Office Action, issued by the United States Patent and Trademark Office in connection with U.S. Appl. No. 12/056,211, on Feb. 16, 2012, 15 pages.
Final Rejection, issued by the United States Patent and Trademark Office in connection with U.S. Appl. No. 12/056,190, on Feb. 17, 2012, 22 pages.
Office Action, issued by the United States Patent and Trademark Office in connection with U.S. Appl. No. 12/122,253, on Feb. 17, 2012, 20 pages.
Office Action, issued by the United States Patent and Trademark Office in connection with U.S. Appl. No. 12/182,874, on Feb. 17, 2012, 15 pages.
First Office Action, issued by the State Intellectual Property Office of P.R. China in connection with Patent Application No. 200880017883.X, on Nov. 30, 2011, 16 pages.
Meriam-Webster Online Dictionary definition for "tangible," available at http://www.meriam-webster.com/dictionary/tangible, 1 page.
Mosby's Dictionary of Medicine, Nursing, & Health Professions, 2009, Mosby, Inc., Definition of Alpha Wave, 1 page.
Mosby's Dictionary of Medicine, Nursing, & Health Professions, 2009, Mosby, Inc., Definition of Beta Wave, 1 page.
U.S. Appl. No. 13/249,512, filed Sep. 30, 2011, (unpublished).
U.S. Appl. No. 13/249,525, filed Sep. 30, 2011, (unpublished).
U.S. Appl. No. 13/288,504, filed Nov. 3, 2011, (unpublished).
U.S. Appl. No. 13/288,571, filed Nov. 3, 2011, (unpublished).
U.S. Appl. No. 12/304,234, filed Nov. 3, 2011, (unpublished).
Final Rejection, issued by the United States Patent and Trademark Office in connection with U.S. Appl. No. 12/056,221, on Nov. 28, 2011, 44 pages.
Office Action, issued by the United States Patent and Trademark Office in connection with U.S. Appl. No. 12/113,863, on Dec. 22, 2011, 17 pages.
Office Action, issued by the United States Patent and Trademark Office in connection with U.S. Appl. No. 12/122,262, on Dec. 22, 2011, 17 pages.
Office Action, issued by the United States Patent and Trademark Office in connection with U.S. Appl. No. 12/199,557, on Dec. 22, 2011, 17 pages.
Office Action, issued by the United States Patent and Trademark Office in connection with U.S. Appl. No. 12/199,596, on Dec. 22, 2011, 15 pages.
Office Action, issued by the United States Patent and Trademark Office in connection with U.S. Appl. No. 12/200,813, on Dec. 22, 2011, 18 pages.
Extended European Search Report, issued by the European Patent Office in connection with European Application No. 11006934.1-2221, on Oct. 25, 2011, 5 pages.
Office Action, issued by the United States Patent and Trademark Office in connection with U.S. Appl. No. 12/199,583, on Dec. 29, 2011, 18 pages.
Final Rejection, issued by the United States Patent and Trademark Office in connection with U.S. Appl. No. 12/410,372, on Jan. 3, 2012, 10 pages.
Final Rejection, issued by the United States Patent and Trademark Office in connection with U.S. Appl. No. 12/413,297, on Jan. 4, 2012, 10 pages.
Office Action, issued by the United States Patent and Trademark Office in connection with U.S. Appl. No. 12/608,660, on Dec. 7, 2011, 43 pages.
Examiner's Answer, issued by the United States Patent and Trademark Office in connection with U.S. Appl. No. 12/234,372, on May 23, 2012, 11 pages.
Advisory Action, issued by the United States Patent and Trademark Office in connection with U.S. Appl. No. 12/234,388, on Aug. 28, 2012, 3 pages.
Examiner's Answer, issued by the United States Patent and Trademark Office in connection with U.S. Appl. No. 12/410,380, on Jun. 8, 2012, 12 pages.
Examiner's Answer, issued by the United States Patent and Trademark Office in connection with U.S. Appl. No. 12/410,372, on Aug. 3, 2012, 8 pages.
Office Action, issued by the United States Patent and Trademark Office in connection with U.S. Appl. No. 12/545,455, on Aug. 29, 2012, 11 pages.
Final Rejection, issued by the United States Patent and Trademark Office in connection with U.S. Appl. No. 12/608,685, on Jul. 30, 2012, 15 pages.
Office Action, issued by the United States Patent and Trademark Office in connection with U.S. Appl. No. 12/778,810, on Aug. 31, 2012, 12 pages.
Office Action, issued by the United States Patent and Trademark Office in connection with U.S. Appl. No. 12/778,828, on Aug. 30, 2012, 9 pages.
Notice of Allowance, issued by the United States Patent and Trademark Office in connection with U.S. Appl. No. 12/056,190, on Sep. 17, 2012, 11 pages.
Notice of Allowance, issued by the United States Patent and Trademark Office in connection with U.S. Appl. No. 12/122,262, on Sep. 17, 2012, 11 pages.
Final Rejection, issued by the United States Patent and Trademark Office in connection with U.S. Appl. No. 12/122,253, on Sep. 17, 2012, 17 pages.
Second Office Action, issued by the State Intellectual Property Office of China in connection with Chinese Patent Application No. 200880017883.X, on Aug. 10, 2012 (9 pages).

Oberman et al., "EEG evidence for mirror neuron activity during the observation of human and robot actions: Toward an analysis of the human qualities of interactive robots," Elsevier, Neurocomputing vol. 70 (2007), Jan. 2, 2007 (10 pages).
Examiner's Answer, issued by the United States Patent and Trademark Office in connection with U.S. Appl. No. 12/413,297, on Sep. 18, 2012, 18 pages.
Final Rejection, issued by the United States Patent and Trademark Office in connection with U.S. Appl. No. 12/546,586, on Sep. 18, 2012, 17 pages.
Notice of Allowance, issued by the United States Patent and Trademark Office in connection with U.S. Appl. No. 12/056,211, on Sep. 19, 2012, 10 pages.
Notice of Allowance, issued by the United States Patent and Trademark Office in connection with U.S. Appl. No. 12/200,813, on Sep. 20, 2012, 11 pages.
Notice of Allowance, issued by the United States Patent and Trademark Office in connection with U.S. Appl. No. 12/853,213, on Sep. 7, 2012, 9 pages.
Notice of Allowance, issued by the United States Patent and Trademark Office in connection with U.S. Appl. No. 12/199,583, on Sep. 26, 2012, 14 pages.
Notice of Allowance, issued by the United States Patent and Trademark Office in connection with U.S. Appl. No. 12/199,596, on Sep. 27, 2012, 14 pages.
English Translation of Office Action, issued by the Israel Patent Office in connection with Patent Application No. 203176, on Sep. 27, 2012, 1 pages.
English Translation of Office Action, issued by the Israel Patent Office in connection with Patent Application No. 203177, on Sep. 27, 2012, 1 pages.
Notice of Allowance, issued by the United States Patent and Trademark Office in connection with U.S. Appl. No. 12/199,557, on Sep. 28, 2012, 12 pages.
Notice of Allowance, issued by the United States Patent and Trademark Office in connection with U.S. Appl. No. 12/113,863, on Oct. 1, 2012, 12 pages.
Office Action, issued by the United States Patent and Trademark Office in connection with U.S. Appl. No. 13/444,149, on Oct. 4, 2012, 9 pages.
Final Office Action, issued by the United States Patent and Trademark Office in connection with U.S. Appl. No. 12/182,851, on Oct. 4, 2012, 14 pages.
Office Action, issued by the United States Patent and Trademark Office in connection with U.S. Appl. No. 12/234,388, on Oct. 5, 2012, 6 pages.
Office Action, issued by the Japanese Patent Office in connection with Patent Application No. 2010-501190, on Oct. 5, 2012, 5 pages.
Notice of Allowance, issued by the United States Patent and Trademark Office in connection with U.S. Appl. No. 12/853,197, on Oct. 16, 2012, 5 pages.
Notice of Allowance, issued by the United States Patent and Trademark Office in connection with U.S. Appl. No. 12/868,531, on Oct. 22, 2012, 5 pages.
English Translation of Office Action, issued by the Japanese Patent Office in connection with Patent Application No. 2010-506646, on Oct. 23, 2012, 3 pages.
Final Office Action, issued by the United States Patent and Trademark Office in connection with U.S. Appl. No. 12/846,242, on Nov. 29, 2012, 14 pages.
Clemons, "Resonance Marketing in the Age of the Truly Informed Consumer: Creating Profits through Differentiation and Delight," Wharton Information Strategy & Economics Blog 2, available at http://opim.wharton.upenn.edu/~clemons/blogs/resonanceblog.pdf, (Mar. 28, 2007), 8 pages.
Notice of Allowance, issued by the United States Patent and Trademark Office in connection with U.S. Appl. No. 12/200,813, on Nov. 2, 2012, 5 pages.
Notice of Allowance, issued by the United States Patent and Trademark Office in connection with U.S. Appl. No. 12/056,190, on Nov. 2, 2012, 5 pages.
Restriction Requirement, issued by the United States Patent and Trademark Office in connection with U.S. Appl. No. 12/056,225, on Nov. 2, 2012, 5 pages.
Final Office Action, issued by the United States Patent and Trademark Office in connection with U.S. Appl. No. 12/135,066, on Nov. 13, 2012, 9 pages.
Notice of Allowance, issued by the United States Patent and Trademark Office in connection with U.S. Appl. No. 12/113,863, on Nov. 16, 2012, 5 pages.
Notice of Allowance, issued by the United States Patent and Trademark Office in connection with U.S. Appl. No. 12/056,211, on Nov. 21, 2012, 5 pages.
Notice of Allowance, issued by the United States Patent and Trademark Office in connection with U.S. Appl. No. 12/868,531, on Nov. 23, 2012, 5 pages.
Office Action, issued by the United States Patent and Trademark Office in connection with U.S. Appl. No. 12/913,102, on Dec. 7, 2012, 7 pages.
Final Office Action, issued by the United States Patent and Trademark Office in connection with U.S. Appl. No. 12/544,958, on Dec. 10, 2012, 16 pages.
Notice of Allowance, issued by the United States Patent and Trademark Office in connection with U.S. Application No. 12/0853,197, on Dec. 20, 2012, 5 pages.
Notice of Allowance, issued by the United States Patent and Trademark Office in connection with U.S. Appl. No. 12/056,190, on Dec. 21, 2012, 14 pages.
Notice of Allowance, issued by the United States Patent and Trademark Office in connection with U.S. Appl. No. 12/056,211, on Dec. 21, 2012, 10 pages.
Notice of Allowance, issued by the United States Patent and Trademark Office in connection with U.S. Appl. No. 12/122,262, on Dec. 21, 2012, 19 pages.
Notice of Allowance, issued by the United States Patent and Trademark Office in connection with U.S. Appl. No. 12/199,557, on Dec. 21, 2012, 14 pages.
Notice of Allowance, issued by the United States Patent and Trademark Office in connection with U.S. Appl. No. 12/199,596, on Dec. 21, 2012, 17 pages.
Notice of Allowance, issued by the United States Patent and Trademark Office in connection with U.S. Appl. No. 12/200,813, on Dec. 21, 2012, 9 pages.
Notice of Allowance, issued by the United States Patent and Trademark Office in connection with U.S. Appl. No. 12/853,213, on Dec. 21, 2012, 10 pages.
Notice of Allowance, issued by the United States Patent and Trademark Office in connection with U.S. Appl. No. 12/868,531, on Dec. 26, 2012, 2 pages.
Notice of Allowance, issued by the United States Patent and Trademark Office in connection with U.S. Appl. No. 12/113,863, on Dec. 31, 2012, 5 pages.
Notice of Allowance, issued by the United States Patent and Trademark Office in connection with U.S. Appl. No. 12/199,583, on Dec. 31, 2012, 10 pages.
Final Office Action, issued by the United States Patent and Trademark Office in connection with U.S. Appl. No. 12/182,874, on Jan. 4, 2013, 17 pages.
Notice of Allowance, issued by the United States Patent and Trademark Office in connection with U.S. Appl. No. 12/199,583, on Jan. 11, 2013, 11 pages.
Final Office Action, issued by the United States Patent and Trademark Office in connection with U.S. Appl. No. 12/056,225, on Jan. 11, 2013, 11 pages.
Recertified IDS and Interview Summary, issued by the United States Patent and Trademark Office in connection with U.S. Appl. No. 12/853,197, on Jan. 16, 2013, 16 pages.
English Translation of Office Action, issued by the Israeli Patent Office in connection with Patent Application No. 201187, on Nov. 27, 2012, 2 pages.
English Translation of Third Office Action, issued by the State Intellectual Property Office of P.R. China in connection with Patent Application No. 200880101500.7, on Nov. 21, 2012, 5 pages.

Extended European Search Report, issued by the European Patent Office in connection with European Application No. 08796890.5-2319/2170161, on Dec. 7, 2012, 9 pages.

Palva et al., "Phase Synchrony Among Neuronal Oscillations in the Human Cortex," Journal of Neuroscience 25 (2005), 3962-3972, 11 pages.

Lachaux et al., "Measuring Phase Synchrony in Brain Signals," Human Brain Mapping 8 (1999), 194-208, 15 pages.

Notice of Allowance, issued by the United States Patent and Trademark Office in connection with U.S. Appl. No. 12/199,557, on Jan. 29, 2013, 17 pages.

Notice of Allowance, issued by the United States Patent and Trademark Office in connection with U.S. Appl. No. 12/853,197, on Jan. 29, 2013, 11 pages.

Notice of Allowance, issued by the United States Patent and Trademark Office in connection with U.S. Appl. No. 12/056,190, on Jan. 31, 2013, 5 pages.

Notice of Allowance, issued by the United States Patent and Trademark Office in connection with U.S. Appl. No. 12/113,863, on Jan. 31, 2013, 5 pages.

Notice of Allowance, issued by the United States Patent and Trademark Office in connection with U.S. Appl. No. 12/199,583, on Feb. 1, 2013, 11 pages.

Notice of Allowance, issued by the United States Patent and Trademark Office in connection with U.S. Appl. No. 12/200,813, on Feb. 1, 2013, 5pages.

Notice of Allowance, issued by the United States Patent and Trademark Office in connection with U.S. Appl. No. 12/056,211, on Feb. 4, 2013, 5 pages.

Notice of Allowance, issued by the United States Patent and Trademark Office in connection with U.S. Appl. No. 12/122,262, on Feb. 5, 2013, 15 pages.

Notice of Allowance, issued by the United States Patent and Trademark Office in connection with U.S. Appl. No. 12/868,531, on Feb. 5, 2013, 8 pages.

Notice of Allowance, issued by the United States Patent and Trademark Office in connection with U.S. Appl. No. 12/853,213, on Feb. 5, 2013, 10 pages.

Notice of Allowance, issued by the United States Patent and Trademark Office in connection with U.S. Appl. No. 12/056,190, on Feb. 14, 2013, 5 pages.

Notice of Allowance, issued by the United States Patent and Trademark Office in connection with U.S. Appl. No. 12/234,388, on Feb. 15, 2013, 9 pages.

Notice of Allowance, issued by the United States Patent and Trademark Office in connection with U.S. Appl. No. 12/182,874, on Apr. 16, 2013, 10 pages.

Notice of Allowance, issued by the United States Patent and Trademark Office in connection with U.S. Appl. No. 12/182,874, on Apr. 22, 2013, 11 pages.

Notification to Grant Patent Right for Invention, issued by the State Intellectual Property Office of P.R. China in connection with Patent Application No. 200880104982.1, on Jan. 14, 2013, 4 pages.

Extended European Search Report, issued by the European Patent Office in connection with European Application No. 08770372.4-1265/2152155, on Feb. 6, 2013, 7 pages.

English Translation of Third Office Action, issued by the State Intellectual Property Office of P.R. China in connection with Patent Application No. 200880017883.X, on Mar. 18, 2013, 8 pages.

Notification to Grant Patent Right for Invention, issued by the State Intellectual Property Office of P.R. China in connection with Patent Application No. 200880101500.7, on Apr. 3, 2013, 2 pages.

Non-Final Office Action, issued by the United States Patent and Trademark Office in connection with U.S. Appl. No. 12/546,586, on Apr. 25, 2013, (34 pages).

Non-Final Office Action, issued by the United States Patent and Trademark Office in connection with U.S. Appl. No. 13/444,149, on May 2, 2013, 27 pages.

Notice of Allowance, issued by the United States Patent and Trademark Office in connection with U.S. Appl. No. 12/056,190, on May 8, 2013, 4 pages.

Notice of Allowance, issued by the United States Patent and Trademark Office in connection with U.S. Appl. No. 12/056,211, on May 8, 2013, 5 pages.

Notice of Allowance, issued by the United States Patent and Trademark Office in connection with U.S. Appl. No. 12/199,596, on May 8, 2013, 7 pages.

Notice of Allowance, issued by the United States Patent and Trademark Office in connection with U.S. Appl. No. 13/569,711, on May 14, 2013, 6 pages.

Notice of Allowance, issued by the United States Patent and Trademark Office in connection with U.S. Appl. No. 12/182,874, on May 17, 2013, 6 pages.

English Translation of Office Action, issued by the Israeli Patent Office in connection with Patent Application No. 203176, on Apr. 23, 2013, 1 page.

Merriam-Webster Online Dictionary, Definition for "Resonance," available at http://www.merriam-webster.com/dictionary/resonance, 4 pages.

Enghoff, Sigurd, Thesis: "Moving ICA and Time-Frequency Analysis in Event-Related EEG Studies of Selective Attention," Technical University of Denmark, (Dec. 1999), 54 pages.

* cited by examiner

AUDIENCE RESPONSE ANALYSIS USING SIMULTANEOUS ELECTROENCEPHALOGRAPHY (EEG) AND FUNCTIONAL MAGNETIC RESONANCE IMAGING (FMRI)

CROSS REFERENCE To RELATED APPLICATIONS

This patent claims priority to Provisional Patent Application 60/942,283 titled Audience Response Analyzer Utilizing Simultaneous EEG and fMRI by Anantha Pradeep, Robert T. Knight, and Ramachandran Gurumoorthy, and filed on Jun. 6, 2007. This patent is related to U.S. patent application Ser. Nos. 12/056,190; 12/056,211; 12/056,221; 12/056,225; 12/113,863; 12/113,870; 12/122,240; 12/122,253; 12/122, 262; 12/135,066; 12/182,851; 12/182,874; 12/199,557; 12/199,583; 12/199,596; 12/200,813; 12/234,372; 12/135, 069; 12/234,388; 12/544,921; 12/544,934; 12/546,586; 12/544,958; 12/846,242; 12/410,380; 12/410,372; 12/413, 297; 12/545,455; 12/608,660; 12/608,685; 13/444,149; 12/608,696; 12/731,868; 13/045,457; 12/778,810; 12/778, 828; 13/104,821; 13/104,840; 12/853,197; 12/884,034; 12/868,531; 12/913,102; 12/853,213; and 13/105,774.

TECHNICAL FIELD

The present disclosure relates to performing audience response analysis using EEG and fMRI.

DESCRIPTION OF RELATED ART

Conventional systems for determining the effectiveness of the stimulus material such as entertainment and marketing rely on either survey based evaluations or limited neurophysiological measurements used in isolation. These conventional systems provide some useful data but are highly inefficient and inaccurate due to a variety of semantic, syntactic, metaphorical, cultural, social, and interpretative errors and biases. The systems and techniques themselves used to obtain neurophysiological measurements are also highly limited.

Consequently, it is desirable to provide improved methods and apparatus for determining the effectiveness of stimulus material.

BRIEF DESCRIPTION OF THE DRAWINGS

The disclosure may best be understood by reference to the following description taken in conjunction with the accompanying drawings, which illustrate particular example embodiments.

DESCRIPTION OF PARTICULAR EMBODIMENTS

Figure 1:
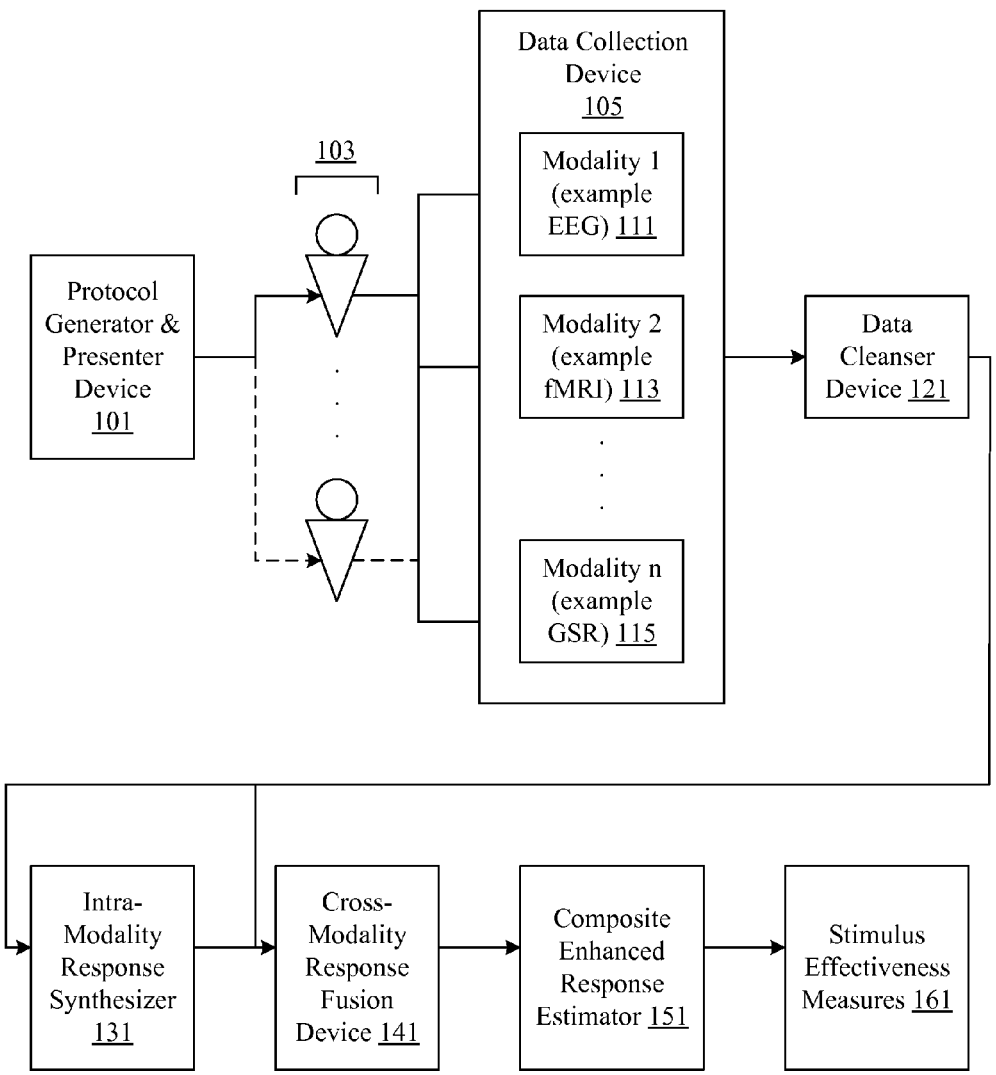
FIG. 1 illustrates one example of a system for determining the effectiveness of marketing and entertainment by using central nervous system, autonomic nervous system, and effector measures.

Reference will now be made in detail to some specific examples of the invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

For example, the techniques and mechanisms of the present invention will be described in the context of EEG and fMRI. However, it should be noted that the techniques and mechanisms of the present invention apply to a variety of modality combinations, and not just EEG and fMRI. In the following description, numerous specific details are set forth in order to provide a thorough understanding of the present invention. Particular example embodiments of the present invention may be implemented without some or all of these specific details. In other instances, well known process operations have not been described in detail in order not to unnecessarily obscure the present invention.

Various techniques and mechanisms of the present invention will sometimes be described in singular form for clarity. However, it should be noted that some embodiments include multiple iterations of a technique or multiple instantiations of a mechanism unless noted otherwise. For example, a system uses a processor in a variety of contexts. However, it will be appreciated that a system can use multiple processors while remaining within the scope of the present invention unless otherwise noted. Furthermore, the techniques and mechanisms of the present invention will sometimes describe a connection between two entities. It should be noted that a connection between two entities does not necessarily mean a direct, unimpeded connection, as a variety of other entities may reside between the two entities. For example, a processor may be connected to memory, but it will be appreciated that a variety of bridges and controllers may reside between the processor and memory. Consequently, a connection does not necessarily mean a direct, unimpeded connection unless otherwise noted.

Overview

Neuro-response data including Electroencephalography (EEG), Functional Magnetic Resonance Imaging (fMRI) is filtered, analyzed, and combined to evaluate the effectiveness of stimulus materials such as marketing and entertainment materials. A data collection mechanism including multiple modalities such as, Electroencephalography (EEG), Functional Magnetic Resonance Imaging (fMRI), Electrooculography (EOG), Galvanic Skin Response (GSR), etc., collects response data from subjects exposed to marketing and entertainment stimuli. A data cleanser mechanism filters the response data and removes cross-modality interference.

Example Embodiments

Conventional mechanisms for obtaining information about the effectiveness of various types of stimuli such as marketing and entertainment materials have generally relied on focus groups and surveys. Subjects are provided with oral and written mechanisms for conveying their thoughts and feelings elicited in response to a particular advertisement, brand, media clip, etc. These oral and written mechanisms provide some limited information on the effectiveness of the marketing and entertainment materials, but have a variety of limitations. For example, subjects may be unable or unwilling to express their true thoughts and feelings about a topic, or questions may be phrased with built in bias. Articulate subjects may be given more weight than nonexpressive ones. A variety of semantic, syntactic, metaphorical, cultural, social and interpretive biases and errors prevent accurate and repeatable evaluation.

Some efforts have been made to use isolated neurological and neurophysiological measurements to gauge subject responses. Some examples of central nervous system measurement mechanisms include Functional Magnetic Resonance Imaging (fMRI) and Electroencephalography (EEG). FMRI measures blood oxygenation in the brain that correlates with increased neural activity. However, current implementations of fMRI have poor temporal resolution of a few seconds. EEG measures electrical activity associated with post synaptic currents occurring in the milliseconds range. Subcranial EEG can measure electrical activity with the most accuracy, as the bone and dermal layers weaken transmission of a wide range of frequencies. Nonetheless, surface EEG provides a wealth of electrophysiological information if analyzed properly.

Autonomic nervous system measurement mechanisms include Galvanic Skin Response (GSR), Electrocardiograms (EKG), pupillary dilation, etc. Effector measurement mechanisms include Electrooculography (EOG), eye tracking, facial emotion encoding, reaction time etc.

Some conventional mechanisms cite a particular neurological or neurophysiological measurement characteristic as indicating a particular thought, feeling, mental state, or ability. For example, one mechanism purports that the contraction of a particular facial muscle indicates the presence of a particular emotion. Others measure general activity in particular areas of the brain and suggest that activity in one portion may suggest lying while activity in another portion may suggest truthfulness. However, these mechanisms are severely limited in their ability to accurately reflect a subject's actual thoughts. It is recognized that a particular region of the brain can not be mapped to a particular thought. Similarly, a particular eye movement can not be mapped to a particular emotion. Even when there is a strong correlation between a particular measured characteristic and a thought, feeling, or mental state, the correlations are not perfect, leading to a large number of false positives and false negatives.

Consequently, the techniques and mechanisms of the present invention intelligently blend multiple modes such as EEG and fMRI to more accurately assess effectiveness of stimulus materials. According to various embodiments, manifestations of precognitive neural signatures are also blended with cognitive neural signatures and post cognitive neurophysiological manifestations to access the effectiveness of marketing and entertainment materials. In some examples, autonomic nervous system measures are themselves used to validate central nervous system measures. Effector and behavior responses are blended and combined with other measures.

Intra-modality measurement enhancements are made in addition to the cross-modality measurement mechanism enhancements. According to various embodiments, brain activity is measured not just to determine the regions of activity, but to determine interactions and types of interactions between various regions. The techniques and mechanisms of the present invention recognize that interactions between neural regions support orchestrated and organized behavior. Thoughts and abilities are not merely based on one part of the brain but instead rely on network interactions between brain regions.

The techniques and mechanisms of the present invention further recognize that different frequency bands used for multi-regional communication can be indicative of the effectiveness of stimuli. For example, associating a name to a particular face may entail activity in communication pathways tuned to particular frequencies. According to various embodiments, select frequency bands are analyzed after filtering. The techniques and mechanisms of the present invention also recognize that high gamma band frequencies have significance. Inter-frequency coupling in the signals have also been determined to indicate effectiveness. Signals modulated on a carrier wave have also been determined to be important in evaluating thoughts and actions. In particular embodiments, the types of frequencies measured are subject and/or task specific. For example, particular types of frequencies in specific pathways are measured if a subject is being exposed to a new product.

In particular embodiments, evaluations are calibrated to each subject and synchronized across subjects. In particular embodiments, templates are created for subjects to create a baseline for measuring pre and post stimulus differentials. According to various embodiments, stimulus generators are intelligent, and adaptively modify specific parameters such as exposure length and duration for each subject being analyzed.

Consequently, the techniques and mechanisms of the present invention provide a central nervous system, autonomic nervous system, and effector measurement and analysis system that can be applied to evaluate the effectiveness of materials such as marketing and entertainment materials. Marketing materials may include advertisements, commercials, media clips, brand messages, product brochures, company logos, etc. An intelligent stimulus generation mechanism intelligently adapts output for particular users and purposes. A variety of modalities can be used including EEG, GSR, EKG, pupillary dilation, EOG, eye tracking, facial emotion encoding, reaction time, etc. Individual modalities such as EEG are enhanced by intelligently recognizing neural region communication pathways. Cross modality analysis is enhanced using a synthesis and analytical blending of central nervous system, autonomic nervous system, and effector signatures. Synthesis and analysis by mechanisms such as time and phase shifting, correlating, and validating intra-modal determinations allow generation of a composite output characterizing the effectiveness of various stimuli.

According to various embodiments, it is recognized that various modalities may be used in sequence. For example, EEG measurements are taken when a subject is exposed to stimulus and fMRI measurements are taken when the subject is again exposed to stimulus. However, exposing subjects in sequence to stimulus and measuring responses using various modalities does not easily account for habituation and wearout. Responses may be significantly different after an initial exposure or after repeated exposures. Consequently, the techniques and mechanisms of the present invention contemplate performing multiple modality measurements simultaneously during a particular exposure to stimulus.

However, performing multiple modality measurements simultaneously presents its own set of problems. For examples, one modality may interfere with the measurements from another modality. For example, EEG wires and electrodes may interfere with fMRI measurements. Consequently, filtering mechanisms are provided to address cross-modality interference, such as interference from EEG wires that disrupt fMRI measurements, or fMRI magnetic fields generating currents that alter EEG measurements. Filtered data is enhanced and combined to provide a blended effectiveness estimate of stimulus material effectiveness.

FIG. 1 illustrates one example of a system for determining the effectiveness of marketing and entertainment by using central nervous system, autonomic nervous system, and effector measures. According to various embodiments, the neuro analysis system includes a protocol generator and presenter device 101. In particular embodiments, the protocol generator and presenter device 101 is merely a presenter device and merely presents stimuli to a user. The stimuli may be a media clip, a commercial, a brand image, a magazine advertisement, a movie, an audio presentation, particular tastes, smells, textures and/or sounds. The stimuli can involve a variety of senses and occur with or without human supervision. Continuous and discrete modes are supported. According to various embodiments, the protocol generator and presenter device 101 also has protocol generation capability to allow intelligent customization of stimuli provided to a subject.

According to various embodiments, the subjects are connected to data collection devices 105. The data collection devices 105 may include a variety of neurological and neurophysiological measurement mechanisms such as EEG, EOG, GSR, EKG, pupilary dilation, eye tracking, facial emotion encoding, and reaction time devices, etc. In particular embodiments, the data collection devices 105 include EEG 111, fMRI 113, and GSR 115. In some instances, only a single data collection device is used. Data collection may proceed with or without human supervision.

The data collection device 105 collects neuro-physiological data from multiple sources. This includes a combination of devices such as central nervous system sources (EEG), autonomic nervous system sources (GSR, EKG, pupilary dilation), and effector sources (EOG, eye tracking, facial emotion encoding, reaction time). In particular embodiments, data collected is digitally sampled and stored for later analysis. In particular embodiments, the data collected could be analyzed in real-time. According to particular embodiments, the digital sampling rates are adaptively chosen based on the neurophysiological and neurological data being measured.

In one particular embodiment, the neurological and neurophysiological analysis system includes EEG 111 measurements made using scalp level electrodes, EOG 113 measurements made using shielded electrodes to track eye data, GSR 115 measurements performed using a differential measurement system, a facial muscular measurement through shielded electrodes placed at specific locations on the face, and a facial affect graphic and video analyzer adaptively derived for each individual.

In particular embodiments, the data collection devices are clock synchronized with a protocol generator and presenter device 101. The data collection system 105 can collect data from a single individual (1 system), or can be modified to collect synchronized data from multiple individuals (N+1 system). The N+1 system may include multiple individuals synchronously tested in isolation or in a group setting. In particular embodiments, the data collection devices also include a condition evaluation subsystem that provides auto triggers, alerts and status monitoring and visualization components that continuously monitor the status of the subject, data being collected, and the data collection instruments. The condition evaluation subsystem may also present visual alerts and automatically trigger remedial actions.

According to various embodiments, the neurological and neurophysiological analysis system also includes a data cleanser device 121. In particular embodiments, the data cleanser device 121 filters the collected data to remove noise, artifacts, and other irrelevant data using fixed and adaptive filtering, weighted averaging, advanced component extraction (like PCA, ICA), vector and component separation methods, etc. This device cleanses the data by removing both exogenous noise (where the source is outside the physiology of the subject) and endogenous artifacts (where the source could be neurophysiological like muscle movement, eye blinks, etc.).

The artifact removal subsystem includes mechanisms to selectively isolate and review the response data and identify epochs with time domain and/or frequency domain attributes that correspond to artifacts such as line frequency, eye blinks, and muscle movements. The artifact removal subsystem then cleanses the artifacts by either omitting these epochs, or by replacing these epoch data with an estimate based on the other clean data (for example, an EEG nearest neighbor weighted averaging approach).

According to various embodiments, the data cleanser device 121 is implemented using hardware, firmware, and/or software. It should be noted that although a data cleanser device 121 is shown located after a data collection device 105 and before synthesis devices 131 and 141, the data cleanser device 121 like other components may have a location and functionality that varies based on system implementation. For example, some systems may not use any automated data cleanser device whatsoever. In other systems, data cleanser devices may be integrated into individual data collection devices.

The data cleanser device 121 passes data to the intra-modality response synthesizer 131. The intra-modality response synthesizer 131 is configured to customize and extract the independent neurological and neurophysiological parameters for each individual in each modality and blend the estimates within a modality analytically to elicit an enhanced response to the presented stimuli. In particular embodiments, the intra-modality response synthesizer also aggregates data from different subjects in a dataset.

According to various embodiments, the cross-modality response synthesis or fusion device 141 blends different intra-modality responses, including raw signals and signals output from synthesizer 131. The combination of signals enhances the measures of effectiveness within a modality. The cross-modality response fusion device 141 can also aggregate data from different subjects in a dataset.

According to various embodiments, the system also includes a composite enhanced response estimator (CERE) that combines the enhanced responses and estimates from each modality to provide a blended estimate of the effectiveness of the marketing and entertainment stimuli for various purposes. Stimulus effectiveness measures are output at 161.

Figure 2:
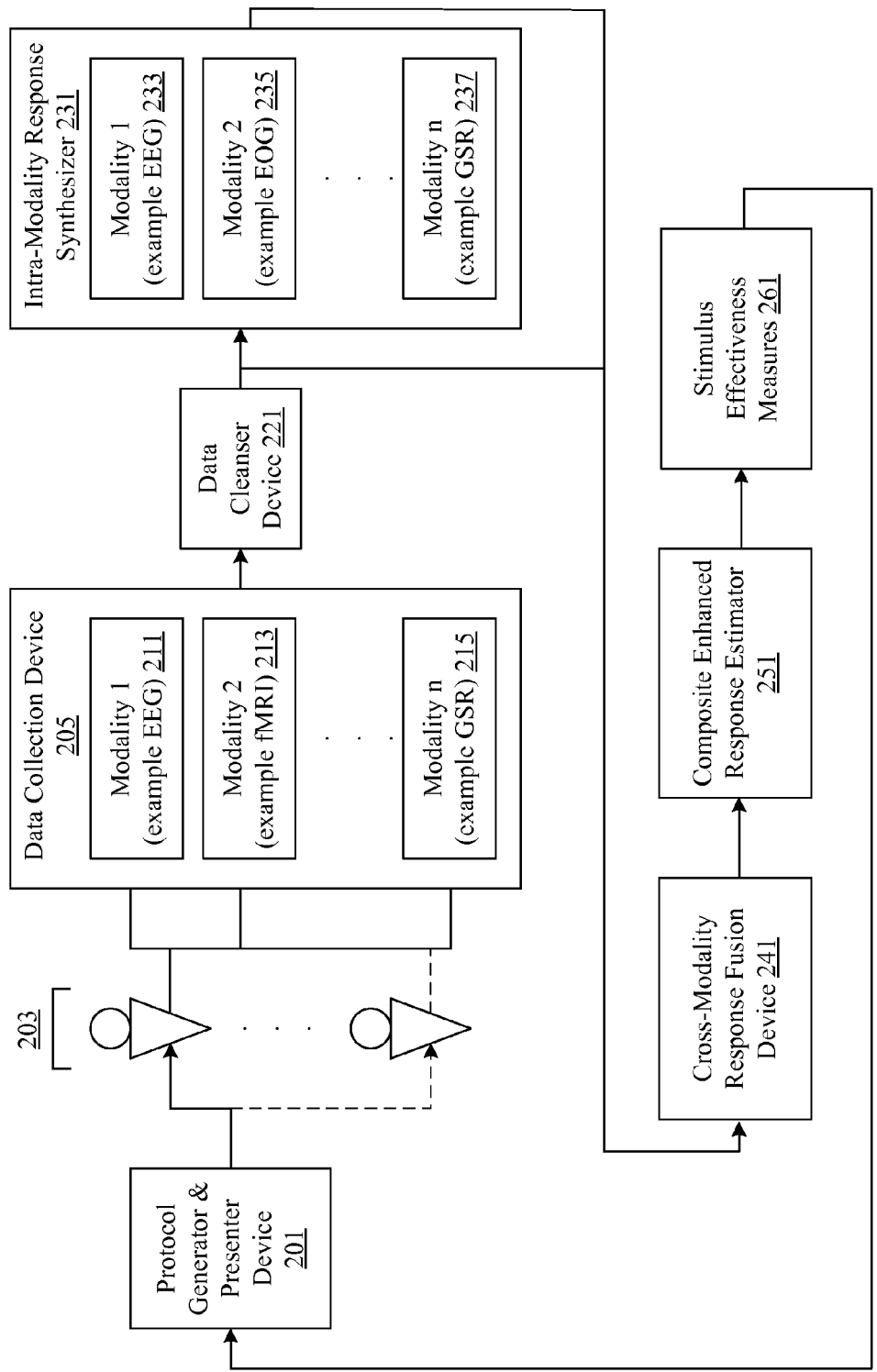
FIG. 2 illustrates a particular example of a system having an intelligent protocol generator and presenter device and individual mechanisms for intra-modality response synthesis.

FIG. 2 illustrates a particular example of a system having an intelligent protocol generator and presenter device (where the intelligence could include a feedback based on prior responses) and individual mechanisms for intra-modality response synthesis.

According to various embodiments, the system includes a protocol generator and presenter device 201. In particular embodiments, the protocol generator and presenter device 201 is merely a presenter device and merely presents preconfigured stimuli to a user. The stimuli may be media clips, commercials, brand images, magazine advertisements, movies, audio presentations, particular tastes, textures, smells, and/or sounds. The stimuli can involve a variety of senses and occur with or without human supervision. Continuous and discrete modes are supported. According to various embodiments, the protocol generator and presenter device 201 also has protocol generation capability to allow intelligent modification of the types of stimuli provided to a subject. In particular embodiments, the protocol generator and presenter device 201 receives information about stimulus effectiveness measures from component 261.

The protocol generator and presenter device 201 dynamical adapts stimuli presentation by using information from the analysis of attention, analysis of emotional engagement, analysis of memory retention, analysis of overall visual, audio, other sensory effectiveness, and ad, show, or content effectiveness, implicit analysis of brand impact, implicit analysis of brand meaning, implicit analysis of brand archetype, implicit analysis of brand imagery, implicit analysis of brand words, explicit analysis of brand impact, explicit analysis of brand meaning, explicit analysis of brand archetype, explicit analysis of brand imagery, explicit analysis of brand words; analysis of characters in the ad, analysis of emotive response to characters in the ad/show/content, analysis of character interaction in the ad/show/content; elicitation of core components of the ad/show/content for print purposes, elicitation of core components of the ad/show/content for billboard purposes; elicitation of the ocular metrics like hotzones in the ad/show/content by eye dwell time, micro and macro saccade separation, saccadic returns to points of interest; elicitation of points for product placement, elicitation of points for logo and brand placement; analysis of game effectiveness, analysis of product placement in games; analysis of website effectiveness, webpage dropoff in a site. According to various embodiments, the information is provided by component 261. In particular embodiments, the protocol generator and presenter device 201 can itself obtain some of this information The protocol generator and presenter device 201 uses a data model along with linguistic and image tools like valence, arousal, meaning matched word/phrase generators, valence and arousal matched image/video selectors to generate parameters regarding the experiment. In particular examples, the protocol generator and presenter device 201 may vary individual presentation parameters like time and duration of the experiment, the number of repetitions of the stimuli based on signal to noise requirements, and the number and repetitions of the stimuli for habituation and wear-out studies, the type and number of neuro-physiological baselines, and the self reporting surveys to include.

In particular examples, the protocol generator and presenter device 201 customizes presentations to a group of subjects or to individual subjects. According to various embodiments, the subjects are connected to data collection devices 205. The data collection devices 205 may involve any type of neurological and neurophysiological mechanism such as EEG, fMRI, EOG, GSR, EKG, pupilary dilation, eye tracking, facial emotion encoding, reaction rime, etc. In particular embodiments, the data collection devices 205 include EEG 211, fMRI 213, and GSR 215. In some instances, only a single modality is used. In other instances, multiple modalities are used and may vary depending on the type of effectiveness evaluation. Data collection may proceed without or without human supervision.

The data collection device 205 automatically collects neuro-physiological data from multiple sources. This includes a combination of devices such as central nervous system sources (EEG, fMRI), autonomic nervous system sources (GSR, EKG, pupillary dilation), and effector sources (EOG, eye tracking, facial emotion encoding, reaction time). In particular embodiments, data collected is digitally sampled and stored for later analysis. The digital sampling rates are adaptively chosen based on the type of neurophysiological and neurological data being measured.

In particular embodiments, the system includes EEG 211 measurements made using scalp level electrodes, EOG 213 measurements made using shielded electrodes to track eye data, GSR 215 measurements performed using a differential measurement system, and a facial affect graphic and video analyzer adaptively derived for each individual.

According to various embodiments, the data collection devices are clock synchronized with a protocol generator and presenter device 201. The data collection system 205 can collect data from a single individual (1 system), or can be modified to collect synchronized data from multiple individuals (N+1 system). The N+1 system could include multiple individuals synchronously recorded in a group setting or in isolation. In particular embodiments, the data collection devices also include a condition evaluation subsystem that provides auto triggers, alerts and status monitoring and visualization components that continuously monitor the status of the data being collected as well as the status of the data collection instruments themselves. The condition evaluation subsystem may also present visual alerts and automatically trigger remedial actions.

According to various embodiments, the system also includes a data cleanser device 221. In particular embodiments, the data cleanser device 221 filters the collected data to remove noise, artifacts, and other irrelevant data using fixed and adaptive filtering, weighted averaging, advanced component extraction (like PCA, ICA), vector and component separation methods, etc. This device cleanses the data by removing both exogenous noise (where the source is outside the physiology of the subject) and endogenous artifacts (where the source could be neurophysiological like muscle movement, eye blinks).

The artifact removal subsystem includes mechanisms to selectively isolate and review the output of each of the data and identify epochs with time domain and/or frequency domain attributes that correspond to artifacts such as line frequency, eye blinks, and muscle movements. The artifact removal subsystem then cleanses the artifacts by either omitting these epochs, or by replacing these epoch data with an estimate based on the other clean data (for example, an EEG nearest neighbor weighted averaging approach), or removes these components from the signal.

According to various embodiments, the data cleanser device 221 is implemented using hardware, firmware, and/or software. It should be noted that although a data cleanser device 221 is shown located after a data collection device 205 and before synthesis devices 231 and 241, the data cleanser device 221 like other components may have a location and functionality that varies based on system implementation. For example, some systems may not use any automated data cleanser device whatsoever. In other systems, data cleanser devices may be integrated into individual data collection devices.

The data cleanser device 221 passes data to the intra-modality response synthesizer 231. The intra-modality response synthesizer is configured to customize and extract the independent neurological and neurophysiological parameters for each individual in each modality and blend the estimates within a modality analytically to elicit an enhanced response to the presented stimuli. In particular embodiments, the intra-modality response synthesizer also aggregates data from different subjects in a dataset. According to various embodiments, various modules perform synthesis in parallel or in series, and can operate on data directly output from a data cleanser device 221 or operate on data output from other modules. For example, EEG synthesis module 233 can operate on the output of EOG synthesis module 235. GSR module 237 can operate on data output from EEG module 233.

According to various embodiments, the cross-modality response synthesis or fusion device 241 blends different intra-modality responses, including raw signals as well as signals output from synthesizer 231. The combination of signals enhances the measures of effectiveness within a modality. The cross-modality response fusion device 241 can also aggregate data from different subjects in a dataset.

According to various embodiments, the neuro analysis system also includes a composite enhanced response estimator (CERE) that combines the enhanced responses and estimates from each modality to provide a blended estimate of the effectiveness of the marketing and advertising stimuli for various purposes. Stimulus effectiveness measures are output at 261. A portion or all of the effectiveness measures (intra-modality synthesizer, cross modality fusion device, and/or the CERE) can be provided as feedback to a protocol generator and presenter device 201 to further customize stimuli presented to users 203.

Figure 3:
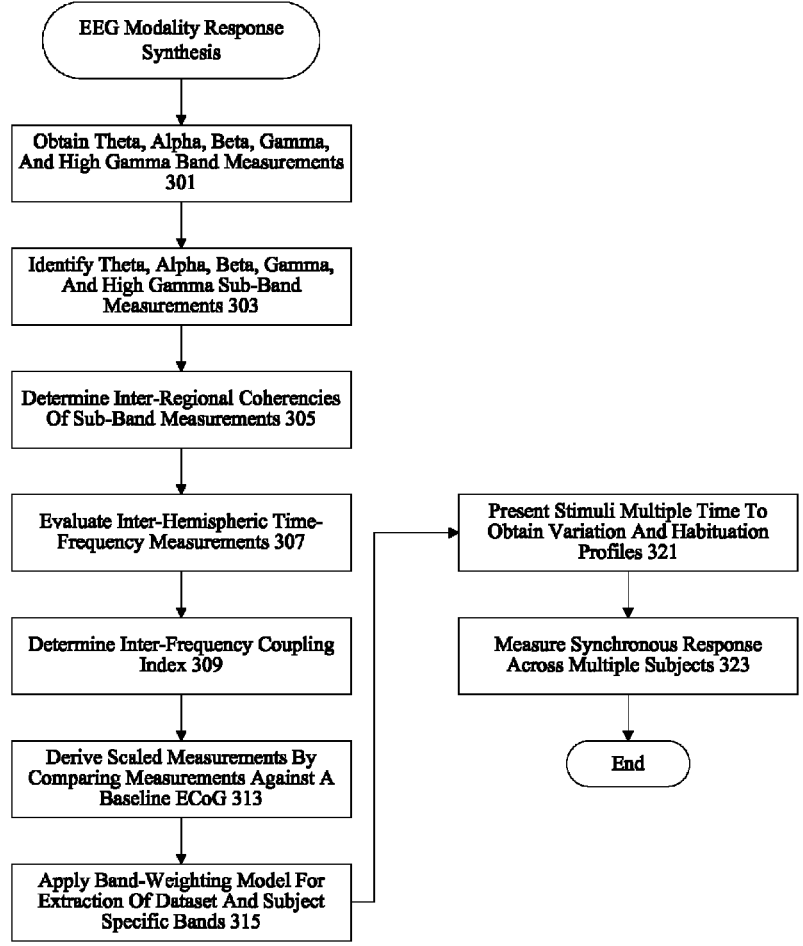
FIG. 3 illustrates a particular example of an intra-modality synthesis mechanism for Electroencephalography (EEG).

FIG. 3 illustrates a particular example of an intra-modality synthesis mechanism. In particular embodiments, EEG response data is synthesized to provide an enhanced assessment of marketing and entertainment effectiveness. According to various embodiments, EEG measures electrical activity resulting from thousands of simultaneous neural processes associated with different portions of the brain. EEG data can be classified in various bands. According to various embodiments, brainwave frequencies includes delta, theta, alpha, beta, and gamma frequency ranges. Delta waves are classified as those less than 4 Hz and are prominent during deep sleep. Theta waves have frequencies between 3.5 to 7.5 Hz and are associated with memories, attention, emotions, and sensations. Theta waves are typically prominent during states of internal focus.

Alpha frequencies reside between 7.5 and 13 Hz and typically peak around 10 Hz. Alpha waves are prominent during states of relaxation. Beta waves have a frequency range between 14 and 30 Hz. Beta waves are prominent during states of motor control, long range synchronization between brain areas, analytical problem solving, judgment, and decision making. Gamma waves occur between 30 and 60 Hz and are involved inbinding of different populations of neurons together into a network for the purpose of carrying out a certain cognitive or motor function, as well as in attention and memory. Because the skull and dermal layers attenuate waves in this frequency range, brain waves above 75-80 Hz are difficult to detect and are often not used for stimuli response assessment.

However, the techniques and mechanisms of the present invention recognize that analyzing high gamma band (kappa-band: Above 60 Hz) measurements, in addition to theta, alpha, beta, and low gamma band measurements, enhances neurological attention, emotional engagement and retention component estimates. In particular embodiments, EEG measurements including difficult to detect high gamma or kappa band measurements are obtained, enhanced, and evaluated at 301. At 303, subject and task specific signature sub-bands in the theta, alpha, beta, gamma and kappa bands are identified to provide enhanced response estimates. According to various embodiments, high gamma waves (kappa-band) above 80 Hz (typically detectable with sub-cranial EEG and magnetoencephalography) can be used in inverse model-based enhancement of the frequency responses to the stimuli.

Various embodiments of the present invention recognize that particular sub-bands within each frequency range have particular prominence during certain activities. A subset of the frequencies in a particular band is referred to herein as a sub-band. For example, a sub-band may include the 40-45 Hz range within the gamma band. In particular embodiments, multiple sub-bands within the different bands are selected while remaining frequencies are band pass filtered. In particular embodiments, multiple sub-band responses may be enhanced, while the remaining frequency responses may be attenuated.

At 305, inter-regional coherencies of the sub-band measurements are determined. According to various embodiments, inter-regional coherencies are determined using gain and phase coherences, Bayesian references, mutual information theoretic measures of independence and directionality, and Granger causality techniques of the EEG response in the different bands, as well as the power measures of (BOLD response in the fMRI and time-frequency response in the EEG response). In particular embodiments, inter-regional coherencies are determined using fuzzy logic to estimate effectiveness of the stimulus in evoking specific type of responses in individual subjects.

At 307, inter-hemispheric time-frequency measurements are evaluated. In particular embodiments, asymmetries in specific band powers, asymmetries in inter-regional intra-hemispheric coherences, and asymmetries in inter-regional intra-hemisphere inter-frequency coupling are analyzed to provide measures of emotional engagement.

At 309, inter-frequency coupling assessments of the response are determined. In particular embodiments, a coupling index corresponding to the measure of specific band activity in synchrony with the phase of other band activity is determined to ascertain the significance of the marketing and advertising stimulus or sub-sections thereof. At 313, a reference scalp power frequency curve is determined using a baseline electrocorticogram (ECOG) power by frequency function driven model. The reference scale power frequency curve is compared to an individual scalp record power by frequency curve to derive scaled estimates of marketing and entertainment effectiveness. According to various embodiments, scaled estimates are derived used fuzzy scaling.

At 315, an information theory based band-weighting model is used for adaptive extraction of selective dataset specific, subject specific, task specific bands to enhance the effectiveness measure. Adaptive extraction may be performed using fuzzy scaling. At 321, stimuli can be presented and enhanced measurements determined multiple times to determine the variation or habituation profiles across multiple presentations. Determining the variation and/or habituation profiles provides an enhanced assessment of the primary responses as well as the longevity (wear-out) of the marketing and entertainment stimuli. At 323, the synchronous response of multiple individuals to stimuli presented in concert is measured to determine an enhanced across subject synchrony measure of effectiveness. According to various embodiments, the synchronous response may be determined for multiple subjects residing in separate locations or for multiple subjects residing in the same location.

Figure 4:
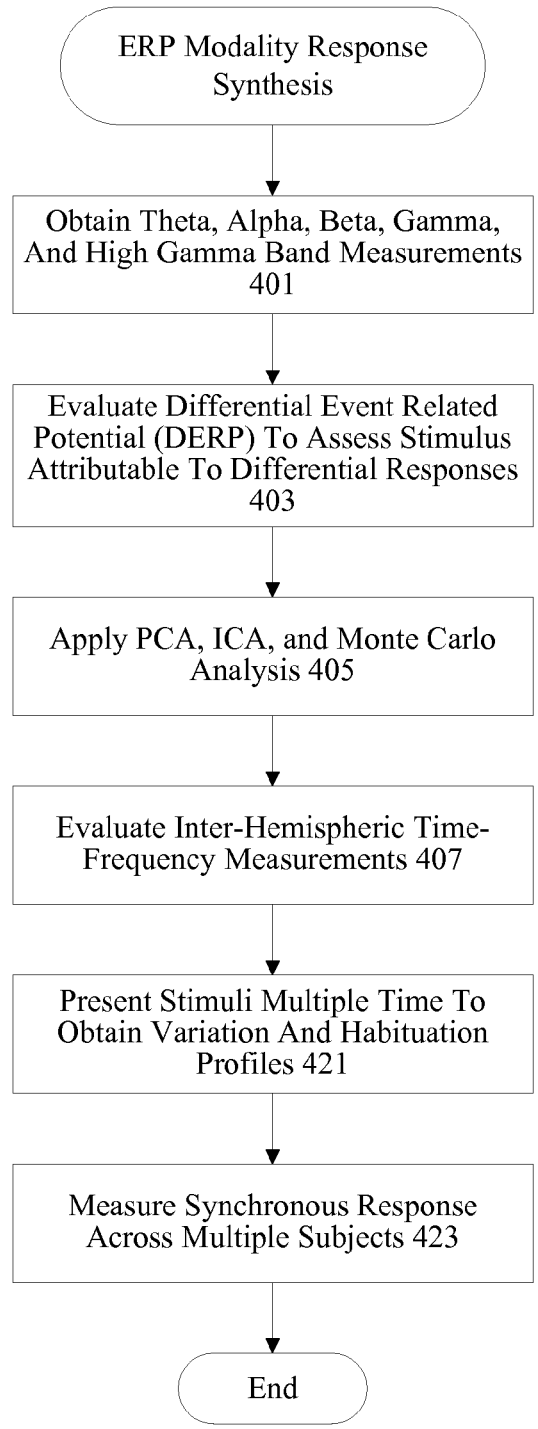
FIG. 4 illustrates another particular example of synthesis for Electroencephalography (EEG).

Although a variety of synthesis mechanisms are described, it should be recognized that any number of mechanisms can be applied—in sequence or in parallel with or without interaction between the mechanisms. In some examples, processes 321 and 323 can be applied to any modality. FIG. 4 illustrates a particular example of synthesis for Electroencephalography (EEG) data, including ERP and continuous EEG.

ERPs can be reliably measured using electroencephalography (EEG), a procedure that measures electrical activity of the brain. Although an EEG reflects thousands of simultaneously ongoing brain processes, the brain response to a certain stimulus may not be visible using EEG. ERP data includes cognitive neurophysiological responses that manifests after the stimulus is presented. In many instances, it is difficult to see an ERP after the presentation of a single stimulus. The most robust ERPs are seen after tens or hundreds of individual presentations are combined. This combination removes noise in the data and allows the voltage response to the stimulus to stand out more clearly. In addition to averaging the embodiment includes techniques to extract single trial evoked information from the ongoing EEG. Using fMRI, block design and event-related BOLD responses of the fMRI can be measured.

While evoked potentials reflect the processing of the physical stimulus, event-related potentials are caused by the "higher" processes, that might involve memory, expectation, attention, or changes in the mental state, among others. According to various embodiments, evidence of the occurrence or non-occurrence of specific time domain components in specific regions of the brain are used to measure subject responsiveness to specific stimulus.

According to various embodiments, ERP data and event-related BOLD responses can be enhanced using a variety of mechanisms. At 401, event related time-frequency analysis of stimulus response—event related power spectral perturbations (ERPSPs)—is performed across multiple frequency bands such as theta, delta, alpha, beta, gamma and high gamma (kappa). According to various embodiments, a baseline ERP is determined. At 403, a differential event related potential (DERP) is evaluated to assess stimulus attributable differential responses.

At 405, a variety of analysis techniques including principal component analysis (PCA), independent component analysis (ICA), and Monte Carlos analysis can be applied to evaluate an ordered ranking of the effectiveness across multiple stimuli. In particular embodiments, PCA is used to reduce multidimensional data sets to lower dimensions for analysis. ICA is typically used to separate multiple components in a signal. Monte Carlo relies on repeated random sampling to compute results. According to various embodiments, an ERP scenario is developed at 407 to determine a subject, session and task specific response baseline. The baseline can then be used to enhance the sensitivity of other ERP responses to the tested stimuli.

At 421, stimuli can be presented and enhanced measurements determined multiple times to determine the variation or habituation profiles across multiple presentations. Determining the variation and/or habituation profiles provides an enhanced assessment of the primary responses as well as the longevity (wear-out) of the marketing and entertainment stimuli. At 423, the synchronous response of multiple individuals to stimuli presented in concert is measured to determine an enhanced across subject synchrony measure of effectiveness. According to various embodiments, the synchronous response may be determined for multiple subjects residing in separate locations or for multiple subjects residing in the same location.

A variety of processes such as processes 421, and 423 can be applied to a number of modalities, including EOG, eye tracking, GSR, facial emotion encoding, etc. In addition, synthesis of data from mechanisms such as EOG and eye tracking can also benefit from the grouping objects of interest into temporally and spatially defined entities using micro and macro saccade patterns. Gaze, dwell, return of eye movements to primarily center around the defined entities of interest and inhibition of return to novel regions of the material being evaluated are measured to determine the degree of engagement and attention evoked by the stimulus.

Figure 5:
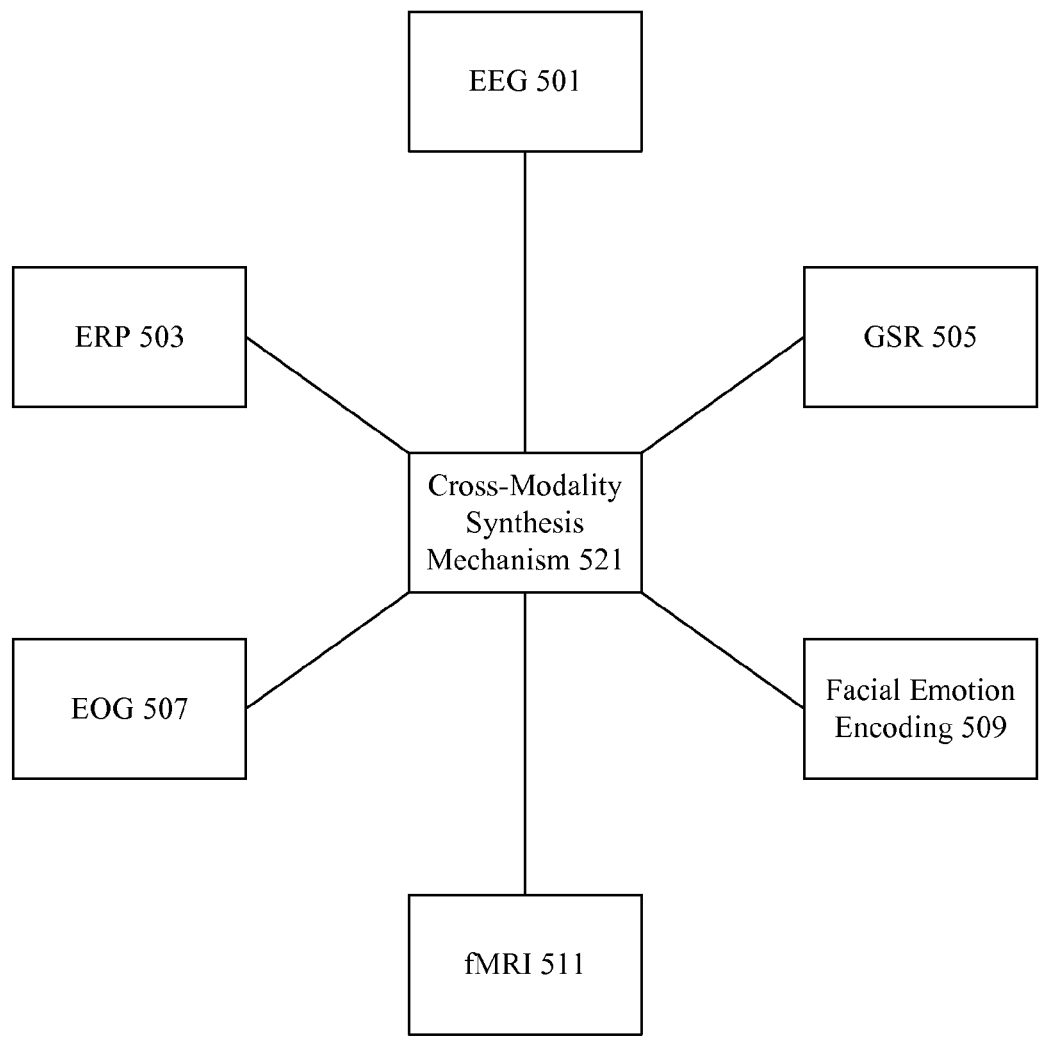
FIG. 5 illustrates a particular example of a cross-modality synthesis mechanism.

Although intra-modality synthesis mechanisms provide enhanced effectiveness data, additional cross-modality synthesis mechanisms can also be applied. FIG. 5 illustrates a particular example of a cross-modality synthesis mechanism. A variety of mechanisms such as EEG 501, Eye Tracking 503, GSR 505, EOG 507, facial emotion encoding 509, and fMRI 511 are connected to a cross-modality synthesis mechanism. Other mechanisms as well as variations and enhancements on existing mechanisms may also be included. According to various embodiments, data from a specific modality can be enhanced using data from one or more other modalities. In particular embodiments, EEG typically makes frequency measurements in different bands like alpha, beta and gamma to provide estimates of effectiveness. However, the techniques of the present invention recognize that effectiveness measures can be enhanced further using information from other modalities.

For example, facial emotion encoding measures can be used to enhance the valence of the EEG emotional engagement measure. EOG and eye tracking saccadic measures of object entities can be used to enhance the EEG estimates of effectiveness including but not limited to attention, emotional engagement, and memory retention. According to various embodiments, a cross-modality synthesis mechanism performs time and phase shifting of data to allow data from different modalities to align. In some examples, it is recognized that an EEG response will often occur hundreds of milliseconds before a facial emotion measurement changes. Correlations can be drawn and time and phase shifts made on an individual as well as a group basis. In other examples, saccadic eye movements may be determined as occurring before and after particular EEG responses. According to various embodiments, time corrected GSR measures are used to scale and enhance the EEG estimates of effectiveness including attention, emotional engagement and memory retention measures.

Evidence of the occurrence or non-occurrence of specific time domain difference event-related potential components (like the DERP) in specific regions correlates with subject responsiveness to specific stimulus. According to various embodiments, ERP measures are enhanced using EEG time-frequency measures (ERPSP) in response to the presentation of the marketing and entertainment stimuli. Specific portions are extracted and isolated to identify ERP, DERP and ERPSP analyses to perform. In particular embodiments, an EEG frequency estimation of attention, emotion and memory retention (ERPSP) is used as a co-factor in enhancing the ERP, DERP and time-domain response analysis.

EOG measures saccades to determine the presence of attention to specific objects of stimulus. Eye tracking measures the subject's gaze path, location and dwell on specific objects of stimulus. According to various embodiments, EOG and eye tracking is enhanced by measuring the presence of lambda waves (a neurophysiological index of saccade effectiveness) in the ongoing EEG in the occipital and extra striate regions, triggered by the slope of saccade-onset to estimate the effectiveness of the EOG and eye tracking measures. In particular embodiments, specific EEG signatures of activity such as slow potential shifts and measures of coherence in time-frequency responses at the Frontal Eye Field (FEF) regions that preceded saccade-onset are measured to enhance the effectiveness of the saccadic activity data.

GSR typically measures the change in general arousal in response to stimulus presented. According to various embodiments, GSR is enhanced by correlating EEG/ERP responses and the GSR measurement to get an enhanced estimate of subject engagement. The GSR latency baselines are used in constructing a time-corrected GSR response to the stimulus. The time-corrected GSR response is co-factored with the EEG measures to enhance GSR effectiveness measures.

According to various embodiments, facial emotion encoding uses templates generated by measuring facial muscle positions and movements of individuals expressing various emotions prior to the testing session. These individual specific facial emotion encoding templates are matched with the individual responses to identify subject emotional response. In particular embodiments, these facial emotion encoding measurements are enhanced by evaluating inter-hemispherical asymmetries in EEG responses in specific frequency bands and measuring frequency band interactions. The techniques of the present invention recognize that not only are particular frequency bands significant in EEG responses, but particular frequency bands used for communication between particular areas of the brain are significant. Consequently, these EEG responses enhance the EMG, graphic and video based facial emotion identification.

Figure 6:
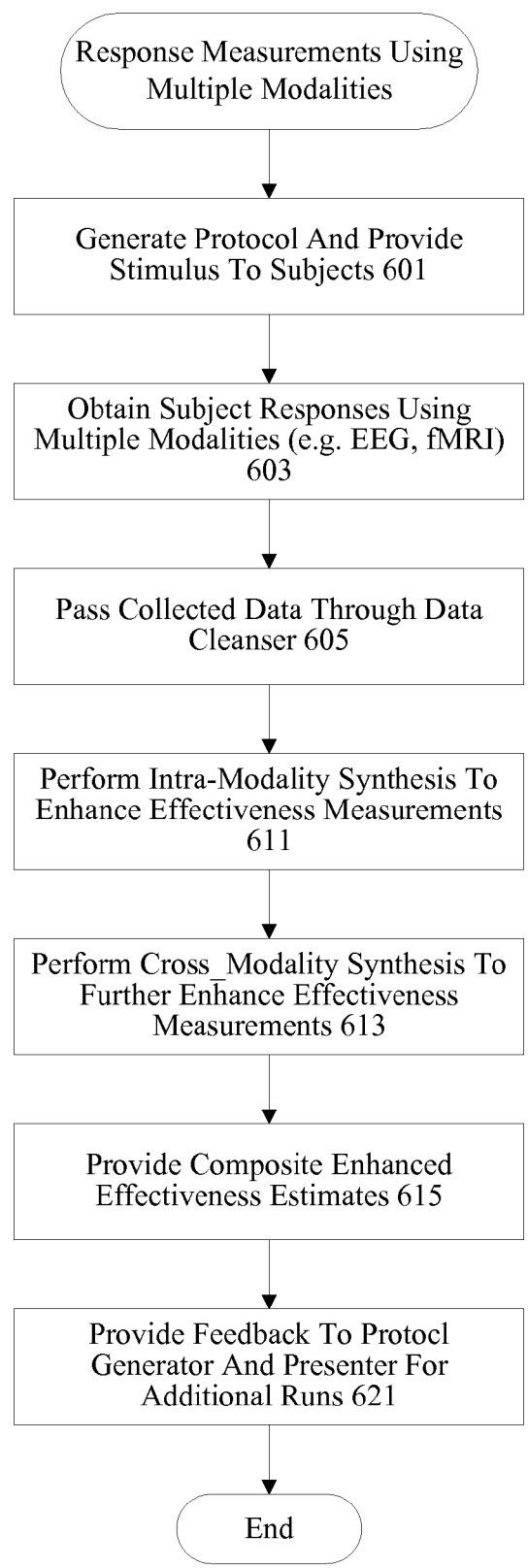
FIG. 6 is one example of a sample flow process diagram showing a technique for obtaining neurological and neurophysiological data.

FIG. 6 is a flow process diagram showing a technique for obtaining neurological and neurophysiological data. At 601, a protocol is generated and stimulus is provided to one or more subjects. According to various embodiments, stimulus includes streaming video, media clips, printed materials, individual products, etc. The protocol determines the parameters surrounding the presentation of stimulus, such as the number of times shown, the duration of the exposure, sequence of exposure, segments of the stimulus to be shown, etc. Subjects may be isolated during exposure or may be presented materials in a group environment with or without supervision. At 603, subject responses are collected using a variety of modalities, such as EEG and fMRI. It should be noted that modalities such as ERP, EOG, GSR, etc., can be used as will. In some examples, verbal and written responses can also be collected and correlated with neurological and neurophysiological responses. At 605, data is passed through a data cleanser to remove noise and artifacts that may make data more difficult to interpret. According to various embodiments, the data cleanser removes EEG electrical activity associated with blinking and other endogenous/exogenous artifacts.

At 611, intra-modality response synthesis is performed to enhance effectiveness measures. At 613, cross-modality response synthesis is performed to further enhance effectiveness measures. It should be noted that in some particular instances, one type of synthesis may be performed without performing other types of synthesis. For example, cross-modality response synthesis may be performed with or without intra-modality synthesis. At 615, a composite enhanced response estimate is provided. At 621, feedback is provided to the protocol generator and presenter device for additional evaluations. This feedback may be provided by the cross-modality response synthesizer or by other mechanisms.

Figure 7:
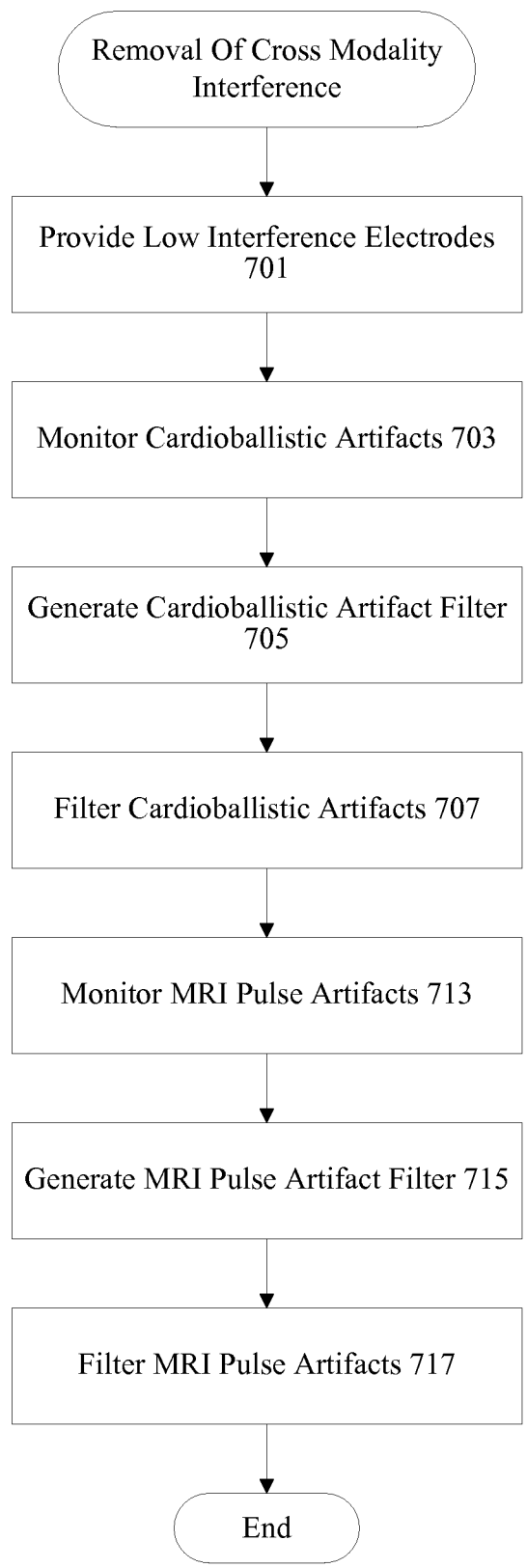
FIG. 7 illustrates a technique for addressing cross-modality interference.

FIG. 7 illustrates one example of a technique for performing cross-modality interference filtering. Obtaining measurements using multiple modalities simultaneously address matters such as habituation and wear-out biases that occur when multiple modalities are used in sequence to measure subject responses. However, using multiple modalities simultaneously may lead to other inaccuracies. For example, electrodes used for EEG may interfere with fMRI measurements. Conventional silver, aluminum, and/or tin electrodes block radio frequency signals and prevent fMRI measurements in a substantial region beneath the electrode. Consequently, the techniques of the present invention provide minimal interference electrodes 701 that do not obstruct fMRI measurements as much as conventional electrodes. For example, sintered ceramic electrodes have leads that allow passage of radio frequency signals through the electrodes. The sintered ceramic electrodes do not block fMRI readings as much as conventional electrodes. EEG wires are also intelligently configured to prevent an antenna effect that absorbs radio frequency signals. In some embodiments, minimal wiring length is provided for the electrodes. Wiring may be twisted, shielded, etc. to minimize antenna effects. In some examples, electrodes may be connected with fibre optic cables or may be connected wirelessly to a receiving device or signal monitor to further reduce the amount of wiring.

According to various embodiments, fMRI magnetic fields can similarly introduce inaccuracies into EEG readings. In particular embodiments, cardioballistic artifacts are filtered. Cardioballistic artifacts are induced by head movements related to cardiac output. The head movements can generate current in the EEG wires when the EEG wires are located in strong magnetic fields such as fMRI induced magnetic fields. Cardioallistic artifacts are significant in comparison to EEG response measurements and can overshadow EEG response measurements. However, cadioballistic artifacts are regular. Consequently, the techniques of the present invention contemplate monitoring cardioballistic artifacts at 703, generating cardioballistic artifact filters at 705, and filtering cardioballistic artifacts at 707. According to various embodiments, cardioballistic artifact filters may be derived for groups or may be derived for individuals.

Pulse artifacts causing small movements in a strong magnetic field can similarly induce strong signals in EEG measurements. According to various embodiments, pulse artifacts are monitored at 713, pulse artifact filters are generated at 715, and pulse artifacts are filtered at 717.

Figure 8:
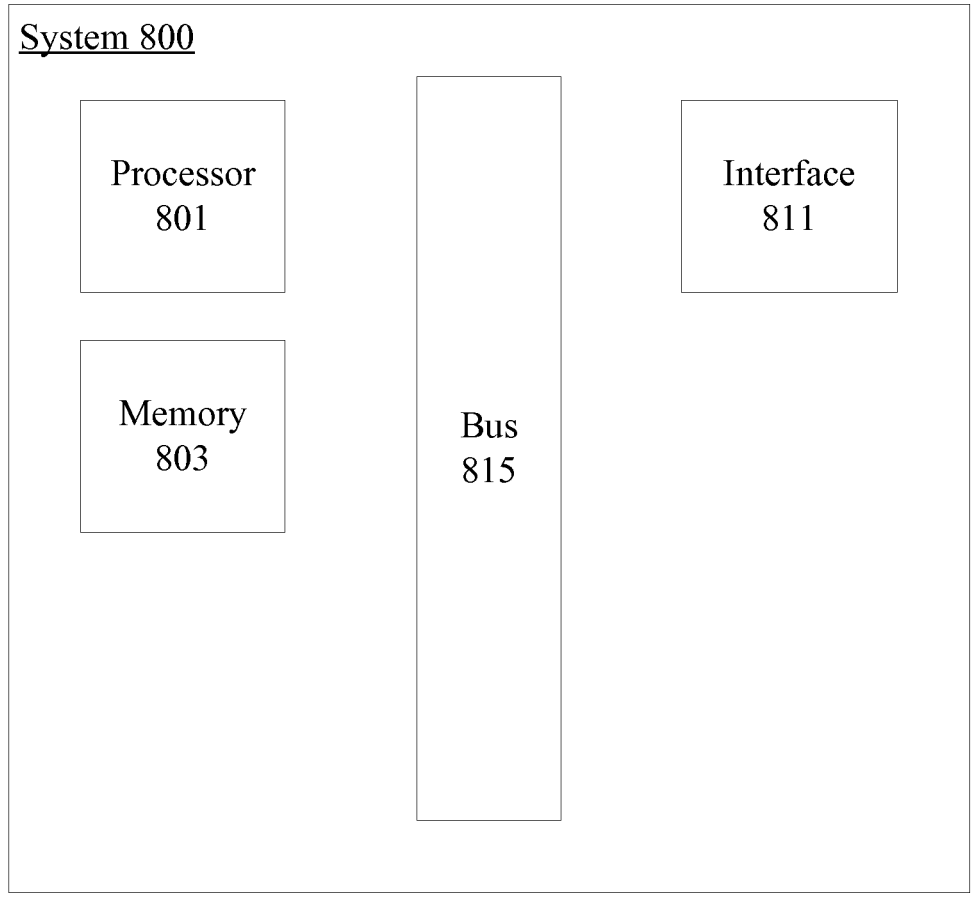
FIG. 8 provides one example of a system that can be used to implement one or more mechanisms.

According to various embodiments, various mechanisms such as the data filtering mechanisms, the data collection mechanisms, the intra-modality synthesis mechanisms, cross-modality synthesis mechanisms, etc. are implemented on multiple devices. However, it is also possible that the various mechanisms are implemented in hardware, firmware, and/or software in a single system. FIG. 8 provides one example of a system that can be used to implement one or more mechanisms. For example, the system shown in FIG. 8 may be used to implement a data cleanser device or a cross-modality responses synthesis device.

According to particular example embodiments, a system 800 suitable for implementing particular embodiments of the present invention includes a processor 801, a memory 803, an interface 811, and a bus 815 (e.g., a PCI bus). When acting under the control of appropriate software or firmware, the processor 801 is responsible for such tasks such as pattern generation. Various specially configured devices can also be used in place of a processor 801 or in addition to processor 801. The complete implementation can also be done in custom hardware. The interface 811 is typically configured to send and receive data packets or data segments over a network. Particular examples of interfaces the device supports include host bus adapter (HBA) interfaces, Ethernet interfaces, frame relay interfaces, cable interfaces, DSL interfaces, token ring interfaces, and the like.

In addition, various very high-speed interfaces may be provided such as fast Ethernet interfaces, Gigabit Ethernet interfaces, ATM interfaces, HSSI interfaces, POS interfaces, FDDI interfaces and the like. Generally, these interfaces may include ports appropriate for communication with the appropriate media. In some cases, they may also include an independent processor and, in some instances, volatile RAM. The independent processors may control such communications intensive tasks as data synthesis.

According to particular example embodiments, the system 800 uses memory 803 to store data, algorithms and program instructions. The program instructions may control the operation of an operating system and/or one or more applications, for example. The memory or memories may also be configured to store received data and process received data.

Because such information and program instructions may be employed to implement the systems/methods described herein, the present invention relates to tangible, machine readable media that include program instructions, state information, etc. for performing various operations described herein. Examples of machine-readable media include, but are not limited to, magnetic media such as hard disks, floppy disks, and magnetic tape; optical media such as CD-ROM disks and DVDs; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

Although the foregoing invention has been described in some detail for purposes of clarity of understanding, it will be apparent that certain changes and modifications may be practiced within the scope of the appended claims. Therefore, the present embodiments are to be considered as illustrative and not restrictive and the invention is not to be limited to the details given herein, but may be modified within the scope and equivalents of the appended claims.

What is claimed is:

1. A system, comprising:
   a data collector to obtain first electroencephalography data from a first frequency band, second electroencephalography data from a second frequency band different than the first frequency band and occurring at a first period in time, and functional magnetic resonance imaging data from a subject exposed to an advertisement or entertainment;
   a filter to remove interference from each of the first electroencephalography data, the second electroencephalography data, and the functional magnetic resonance imaging data;
   an intra-modality response synthesizer comprising a processor configured to:
     detect a first pattern of oscillation in the first frequency band;
     detect a second pattern of oscillation in the second frequency band;
     generate, using a processor configured to, a coupling index based on a phase synchrony between the first frequency band and the second frequency band, wherein the phase synchrony is determined by detecting a repeating sequence of relative phase angles between the first pattern of oscillation in the first frequency band and the second pattern of oscillation in the second frequency band; and
   a cross-modality response synthesizer to analyze the coupling index and the functional magnetic resonance imaging data to evaluate effectiveness of the advertisement or entertainment at the first period in time.

2. The system of claim 1, wherein the filter is to remove electroencephalography generated artifacts from the functional magnetic resonance imaging data and to remove functional magnetic resonance imaging generated artifacts from at least one of the first or second electroencephalography data.

3. The system of claim 1, wherein the cross-modality response synthesizer is to align the functional magnetic resonance imaging data with at least one of the first electroencephalography data or the second electroencephalography data by at least one of time shifting or phase shifting at least one of the first electroencephalography data, the second electroencephalography data or the functional magnetic resonance imaging data.

4. The system of claim 1, wherein the data collector is to obtain electrooculography data.

5. The system of claim 1, wherein the data collector is to obtain eye tracking data.

6. The system of claim 5, wherein the cross-modality response synthesizer is to align the eye tracking data with at least one of the first electroencephalography data or the second electroencephalography data and to combine the aligned data.

7. The system of claim 1, wherein the data collector is to obtain galvanic skin response data.

8. The system of claim 7, wherein the cross-modality response synthesizer is to align the galvanic skin response data with at least one of the first electroencephalography data or the second electroencephalography data and to combine the aligned data.

9. The system of claim 1, wherein the intra-modality response synthesizer is to combine the first electroencephalography data and the second electroencephalography data to determine single trial evoked information.

10. A method, comprising:
    obtaining, with a plurality of sensors, first electroencephalography data from a first frequency band, second electroencephalography data from a second frequency band different than the first frequency band and occurring at a first period in time, and functional magnetic resonance imaging data from a subject exposed to an advertisement or entertainment;
    filtering interference from the first electroencephalography data, the second electroencephalography data, and the functional magnetic resonance imaging data;
    detecting a first pattern of oscillation in the first frequency band;
    detecting a second pattern of oscillation in the second frequency band;
    generating, using a processor, a coupling index based on a phase synchrony between the first frequency band and the second frequency band, wherein the phase synchrony is determined by detecting a repeating sequence of relative phase angles between the first pattern of oscillation in the first frequency band and the second pattern of oscillation in the second frequency band; and
    analyzing the coupling index and the functional magnetic resonance imaging data to evaluate effectiveness of the advertisement or entertainment at the first period in time.

11. The method of claim 10, wherein filtering the interferences comprises:
   filtering electroencephalography generated artifacts from the functional magnetic resonance imaging data; and
   filtering functional magnetic resonance imaging generated artifacts from at least one of the first or second electroencephalography data.

12. The method of claim 10 further comprising aligning the functional magnetic resonance imaging data with at least one of the first electroencephalography data or the second electroencephalography data by at least one of time shifting or phase shifting at least one of the first electroencephalography data, the second electroencephalography data or the functional magnetic resonance imaging data.

13. The method of claim 10 further comprising obtaining electrooculography data.

14. The method of claim 10 further comprising obtaining eye tracking data.

15. The method of claim 14 further comprising:
   aligning the eye tracking data with at least one of the first electroencephalography data or the second electroencephalography data; and
   combining the aligned data.

16. The method of claim 10 further comprising obtaining galvanic skin response data.

17. The method of claim 16 further comprising:
   aligning the galvanic skin response data with at least one of the first electroencephalography data or the second electroencephalography data; and
   combining the aligned data.

18. The method of claim 10 further comprising combining the first electroencephalography data and the second electroencephalography data to determine single trial evoked information.

19. A tangible machine readable storage device or disc comprising machine readable instructions thereon which, when read, cause a machine to at least:
   filter interference from first electroencephalography data obtained from a first frequency band, second electroencephalography data obtained from a second frequency band different than the first frequency band and occurring at same period in time, and functional magnetic resonance imaging data, the first electroencephalography data, the second electroencephalography data and the functional magnetic resonance imagining data obtained from a subject exposed to an advertisement or entertainment;
   detect a first pattern of oscillation in the first frequency band;
   detect a second pattern of oscillation in the second frequency band;
   generate a coupling index based on a phase synchrony between the first frequency band and the second frequency band, wherein the phase synchrony is determined by detecting a repeating sequence of relative phase angles between the first pattern of oscillation in the first frequency band and the second pattern of oscillation in the second frequency band; and
   analyze the coupling index and the functional magnetic resonance imaging data to evaluate effectiveness of the advertisement or entertainment at the first period in time.

20. The machine readable device or disc of claim 19, wherein the instructions further cause the machine to:
   filter electroencephalography generated artifacts from the functional magnetic resonance imaging data; and
   filter functional magnetic resonance imaging generated artifacts from at least one of the first or second electroencephalography data.

* * * * *